(12) United States Patent
Ohmura

(10) Patent No.: US 11,317,801 B2
(45) Date of Patent: May 3, 2022

(54) OPHTHALMIC APPARATUS

(71) Applicant: NIKON CORPORATION, Tokyo (JP)

(72) Inventor: Yasuhiro Ohmura, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 227 days.

(21) Appl. No.: 16/664,118

(22) Filed: Oct. 25, 2019

(65) Prior Publication Data

US 2020/0054211 A1 Feb. 20, 2020

Related U.S. Application Data

(63) Continuation of application No. PCT/JP2018/015614, filed on Apr. 13, 2018.

(30) Foreign Application Priority Data

Apr. 28, 2017 (JP) .............................. JP2017-089977

(51) Int. Cl.
*A61B 3/12* (2006.01)
*A61B 3/10* (2006.01)
(Continued)

(52) U.S. Cl.
CPC ............ *A61B 3/1225* (2013.01); *A61B 3/102* (2013.01); *A61B 3/125* (2013.01); *A61B 3/107* (2013.01)

(58) Field of Classification Search
CPC ..... A61B 3/103; A61B 3/1015; A61B 3/0091; A61B 3/14; A61B 3/0025; A61B 3/1005; A61B 3/12; A61B 3/102; A61B 3/107; A61B 3/0008; A61B 3/1035; A61B 3/10; A61B 3/1025; A61B 3/152; A61B 3/0041; A61B 3/032; A61B 3/1225; A61B 3/165; A61B 3/028; A61B 3/036; G01B 9/02091;
(Continued)

(56) References Cited

U.S. PATENT DOCUMENTS

| 4,003,642 A | 1/1977 | Vogeley |
| 5,004,331 A | 4/1991 | Haseltine |

(Continued)

FOREIGN PATENT DOCUMENTS

| JP | 2000-504251 A | 4/2000 |
| JP | 2000-206410 A | 7/2000 |

(Continued)

OTHER PUBLICATIONS

English translation of Office Action issued in corresponding Chinese Patent Application No. 201880028112.4 dated Apr. 27, 2021.

*Primary Examiner* — William R Alexander
*Assistant Examiner* — Sharrief I Broome
(74) *Attorney, Agent, or Firm* — Foley & Lardner LLP

(57) ABSTRACT

A wide range within a subject eye is observed while a burden on a subject of whom the subject eye is part is moderated. In an optical system that deals with light reflected from the fundus of the subject eye, a first optical system that pertains to a field of view of a fundus central portion centered on an optical axis is used as a standard optical system. The optical system can be switched by a replacement mechanism from the first optical system to a second optical system that pertains to a field of view of a fundus surroundings portion surrounding the fundus central portion.

14 Claims, 25 Drawing Sheets

(51) Int. Cl.
*A61B 3/125* (2006.01)
*A61B 3/107* (2006.01)

(58) Field of Classification Search
CPC .............. G01B 9/0203; G01B 2290/70; G01B 9/02044; G01B 9/02069; G01B 9/02077; G01B 11/026; G01B 11/14; G01B 11/306; G01B 2290/45; G01B 2290/60; G01B 2290/65; G01B 9/02004; G01B 9/02014; G01B 9/02027; G01B 9/02032; G01B 9/02036; G01B 9/02039; G01B 9/02041; G01B 9/02043; A61F 9/008; A61F 2009/00872; A61F 2009/0088; A61F 2009/00848; A61F 9/007; A61F 9/00804; A61F 9/00806; A61F 2009/00846; A61F 2009/00855; A61F 2009/00863; A61F 2009/0087; A61F 2009/00895; A61F 2009/00897; A61F 9/00802; A61F 9/00821; A61F 9/00827; A61F 9/0136

See application file for complete search history.

(56) References Cited

U.S. PATENT DOCUMENTS

| | | | |
|---|---|---|---|
| 6,164,779 A * | 12/2000 | Volk | A61B 3/125 351/219 |
| 6,473,243 B1 | 10/2002 | Omura | |
| 6,621,557 B2 | 9/2003 | Takahashi | |
| 2001/0038446 A1* | 11/2001 | Takahashi | G03F 7/70233 355/67 |
| 2011/0143287 A1* | 6/2011 | Ohmura | G03F 7/70341 430/325 |
| 2013/0093996 A1 | 4/2013 | Thomson | |
| 2013/0293837 A1* | 11/2013 | Akiba | A61B 3/165 351/205 |
| 2019/0261851 A1* | 8/2019 | Williamson | A61B 3/102 |

FOREIGN PATENT DOCUMENTS

| | | |
|---|---|---|
| JP | 3346775 B2 | 11/2002 |
| JP | 2013-524978 A | 6/2013 |
| WO | WO-1998/017170 A1 | 4/1998 |
| WO | WO-2012/095620 A1 | 7/2012 |

* cited by examiner

OPHTHALMIC APPARATUS

CROSS-REFERENCE TO RELATED APPLICATION

This application is a continuation application of International Application No. PCT/JP2018/015614, filed Apr. 13, 2018, the disclosure of which is incorporated herein by reference in its entirety. Further, this application claims priority from Japanese Patent Application No. 2017-089977, filed Apr. 28, 2017, the disclosure of which is incorporated herein by reference in its entirety.

TECHNICAL FIELD

The disclosed technology relates to an ophthalmic apparatus.

BACKGROUND ART

In ophthalmology, a number of ophthalmic imaging apparatuses have been realized that enable observation of the interior of the eye of a subject (below referred to as "the subject eye"), particularly the fundus region of the subject eye, for purposes of eye examinations and surgical treatment of eyes. For example, a technology is known (see Patent Document 1) that relates to an observation apparatus that creates a real image of the fundus of the subject eye. In the present Description, the meaning of the term "ophthalmic" is intended to include fields of medicine relating to the eyes.

In the technology recited in Patent Document 1, a lens element featuring a concave rear surface with a shape that matches the curvature of the cornea is put into close contact with the subject eye (the cornea), and an optical system including this close-contact lens element is configured to form a real image of the fundus region of the subject eye.

RELATED ART REFERENCES

Patent Documents

Patent Document 1: Japanese Patent Application National Publication No. 2000-504251

SUMMARY OF INVENTION

Technical Problem

The disclosed technology provides an ophthalmic apparatus that, compared to a situation in which a lens element is put into close contact with a subject eye and the interior of the subject eye is observed, both may moderate a burden on a subject of whom the subject eye is part and may enable observation of a wide range within the subject eye.

Solution to Problem

An ophthalmic apparatus according to a first aspect of the disclosed technology includes: a first optical system that acquires an image of a predetermined region of a subject eye; and a second optical system that includes a catadioptric optical unit and that acquires an image of a surrounding portion of the predetermined region.

In an ophthalmic apparatus according to a second aspect, in the ophthalmic apparatus according to the first aspect, the catadioptric optical unit includes: a first reflection surface that includes an aperture portion centered on an optical axis of the ophthalmic apparatus and reflects light from the subject eye; and a second reflection surface that includes an aperture portion centered on the optical axis of the ophthalmic apparatus and reflects light reflected from the first reflection surface, the second reflection surface reflecting the light to the opposite side from a side of the second reflection surface at which the subject eye is disposed.

In an ophthalmic apparatus according to a third aspect, in the ophthalmic apparatus according to the second aspect, the first optical system and the second optical system form a pupil conjugate position that is conjugate with a position of a pupil of the subject eye at a position at an opposite side of the first optical system and second optical system from sides of the first and second optical system thereof at which the subject eye is disposed.

In an ophthalmic apparatus according to a fourth aspect, in the ophthalmic apparatus according to the first aspect, the first optical system includes a first optical unit and a rear optical unit, and the second optical system includes the catadioptric optical unit and the rear optical unit.

In an ophthalmic apparatus according to a fifth aspect, the ophthalmic apparatus according to the fourth aspect further includes a replacement device that replaces the first optical unit with the catadioptric optical unit.

In an ophthalmic apparatus according to a sixth aspect, in the ophthalmic apparatus according to the first aspect, the first optical system includes a first optical unit and a rear optical unit, and the second optical system includes the catadioptric optical unit and a rear optical unit that differs from the rear optical unit of the first optical system.

In an ophthalmic apparatus according to a seventh aspect, the ophthalmic apparatus according to the sixth aspect further includes a replacement device that replaces the first optical system with the second optical system.

In an ophthalmic apparatus according to an eighth aspect, in the ophthalmic apparatus according to the first aspect, the shape of the image of the surrounding portion is an annular shape centered on the optical axis of the ophthalmic apparatus.

In an ophthalmic apparatus according to a ninth aspect, in the ophthalmic apparatus according to the eighth aspect, the predetermined region contains the optical axis, and there is an overlap between the image of the predetermined region according to the first optical system and the annular image of the surrounding portion of the predetermined region according to the second optical system, the overlap including a boundary between the images.

In an ophthalmic apparatus according to a tenth aspect, in the ophthalmic apparatus according to the third aspect, the first optical system and the second optical system satisfy the conditional expression:

$$0.2 < \beta 1 \cdot (1-M2)/\beta 2 \cdot (1-M1) < 1.0$$

where in $\beta 1$ represents an imaging magnification of the first optical system between a pupil position of the subject eye and a pupil conjugate position, M1 represents a distortion factor of a maximum field of view of a fundus conjugate image when an aplanatic ideal lens is included at the pupil conjugate position, $\beta 2$ represents an imaging magnification of the second optical system between the pupil position of the subject eye and the pupil conjugate position, and M2 represents a distortion factor of the maximum field of view of the fundus conjugate image when the aplanatic ideal lens is included at the pupil conjugate position.

In an ophthalmic apparatus according to an eleventh aspect, in the ophthalmic apparatus according to the tenth aspect, β1, β2, M1 and M2 satisfy the conditional expressions:

$$2 < \beta 1/(1-M1) < 13$$

$$9 < \beta 2/(1-M2) < 17.$$

In an ophthalmic apparatus according to a twelfth aspect, in the ophthalmic apparatus according to the first aspect, the second optical system is configured to enable incidence of light from the pupil of the subject eye into the catadioptric optical unit with an external illumination angle of at least 100°.

In an ophthalmic apparatus according to a thirteenth aspect, in the ophthalmic apparatus according to the first aspect, optical elements of the first optical system and the second optical system are respectively aligned on a single optical axis.

In an ophthalmic apparatus according to a fourteenth aspect, in the ophthalmic apparatus according to the first aspect, each of the first optical system and the second optical system includes a common lens group with a positive refractive power overall, the common lens group including at least one surface with a negative refractive power.

In an ophthalmic apparatus according to a fifteenth aspect, in the ophthalmic apparatus according to the third aspect, the ophthalmic apparatus satisfies the conditional expression:

$$0.8 < L1/L2 < 1.2$$

where in L1 represents a distance from a pupil position of the subject eye to a pupil conjugate position with respect to the first optical system, and L2 represents a distance from the pupil position of the subject eye to a pupil conjugate position with respect to the second optical system.

In an ophthalmic apparatus according to a sixteenth aspect, in the ophthalmic apparatus according to the first aspect, the ophthalmic apparatus satisfies the conditional expression:

$$1.0 \leq H1/H2 < 5.0$$

where in H1 represents an effective aperture diameter of the first optical system in the plane of a pupil position at the subject eye, and H2 represents an effective aperture diameter of the second optical system in the plane of the pupil position at the subject eye.

DETAILED DESCRIPTION

Below, an exemplary embodiment is described with reference to the attached drawings.

Figure 1:
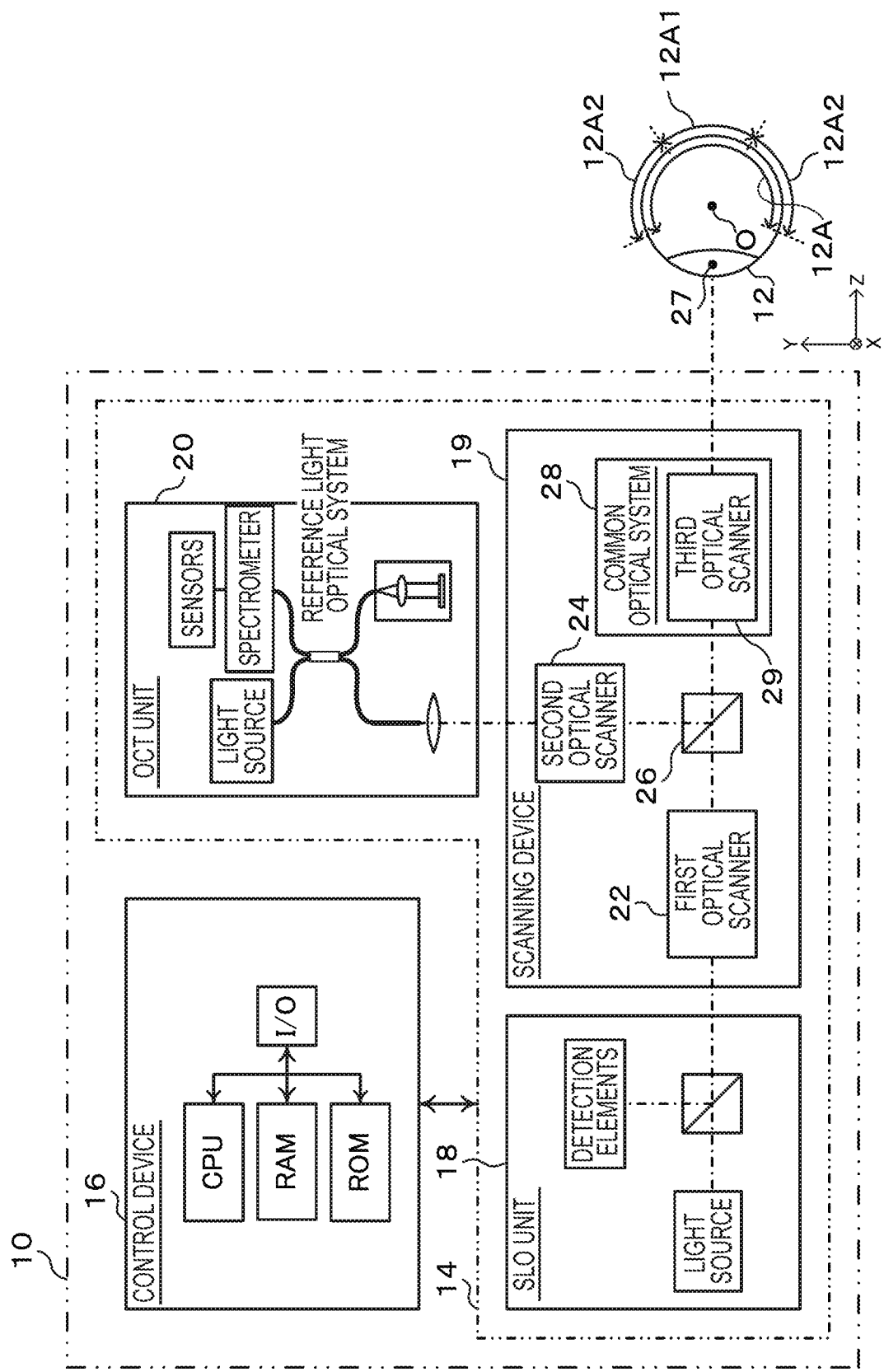
FIG. 1 is a block diagram showing an example of overall structure of an ophthalmic imaging apparatus according to an exemplary embodiment.

FIG. 1 shows an example of structure of an ophthalmic imaging apparatus 10 according to the present exemplary embodiment.

As shown in FIG. 1, the ophthalmic imaging apparatus 10 includes an apparatus main body 14, which images the fundus of a subject eye, and a control device 16. In the descriptions below, the meaning of the term "imaging" is intended to include a user using the ophthalmic imaging apparatus 10 to acquire an image showing a subject body, for which the term "capturing an image" may be used. The apparatus main body 14 operates under the control of the control device 16. The apparatus main body 14 includes an SLO unit 18, a scanning device 19 and an OCT unit 20.

In the descriptions below, a horizontal direction when the ophthalmic imaging apparatus 10 is placed on a horizontal surface is referred to as "the X direction", a direction perpendicular to the horizontal direction is referred to as "the Y direction", and a direction from an anterior portion of a subject eye 12 through the eyeball center O toward the fundus is referred to as "the Z direction". Thus, the X direction is a direction that is orthogonal to both the Y direction and the Z direction.

As an example of principal functions that can be implemented by the ophthalmic imaging apparatus 10, the ophthalmic imaging apparatus 10 according to the present exemplary embodiment features two functions. A first function is a function that causes the ophthalmic imaging apparatus 10 to operate as a scanning laser ophthalmoscope (SLO) and capture images by SLO imaging (below referred to as "the SLO imaging system function"). The second function is a function that causes the ophthalmic imaging apparatus 10 to operate as an optical coherence tomography (OCT) apparatus and capture images by OCT imaging (below referred to as "the OCT imaging system function").

The SLO imaging system function is implemented by, among structures of the ophthalmic imaging apparatus 10, the control device 16, the SLO unit 18 and the scanning device 19, which includes a first optical scanner 22. The SLO unit 18 includes a light source, detection elements and so forth, and is capable of imaging the fundus of the subject eye 12. That is, by operating as the SLO imaging system function, the ophthalmic imaging apparatus 10 images a subject body that is (for example, an imageable region 12A of) the fundus of the subject eye 12. More specifically, light from the SLO unit 18 (below referred to as SLO light) is passed through the pupil of the subject eye 12 by the scanning device 19 and is scanned relative to the imageable region 12A in the Y direction (a vertical direction) by the first scanner 22 and in the X direction (a horizontal direction) by a third scanner 29, and an image of reflected light is acquired by the SLO unit 18. The SLO imaging system function is a widely known function. Accordingly, the SLO imaging system function is not described in detail here.

The OCT imaging system function is implemented by the control device 16, the OCT unit 20 and the scanning device 19, which includes a second optical scanner 24. The OCT unit 20 includes a light source, a spectrometer, sensors, an illuminating optical system and so forth, and is capable of imaging plural tomographic regions in the tissue thickness direction of the fundus. That is, by operating as the OCT imaging system function, the ophthalmic imaging apparatus 10 images tomographic regions that are regions in the tissue thickness direction of the fundus (for example, of the imageable region 12A). More specifically, light from the OCT unit 20 (below referred to as measurement light) is passed through the pupil of the subject eye 12 by the scanning device 19 and is scanned relative to the imageable region 12A in the Y direction (the vertical direction) by the second scanner 24 and in the X direction (the horizontal direction) by the third scanner 29. Reflected light of the measurement light is interfered with reference light to produce interference light. The OCT unit 20 detects spectral components of the interference light, and the control device 16 uses the detection results to acquire physical quantities (for example, a tomography image) representing a tomographic region. The OCT imaging system function is a widely known function. Accordingly, the OCT imaging system function is not described in detail here.

In the following descriptions, because the SLO light and the measurement light are both scanned two-dimensionally in the X direction and the Y direction, where there is no need to distinguish between the SLO light and the measurement light, the SLO light and the measurement light are collectively referred to as "scanned light".

In the present exemplary embodiment, an example of the ophthalmic imaging apparatus 10 including functions that utilize scanned light is described. However, the ophthalmic imaging apparatus featuring functions that utilize scanned light is not limiting; it is sufficient to include functions that enable observation of the subject eye 12. For example, illumination of scanned light is not limiting; an ophthalmic imaging apparatus featuring a function that illuminates light onto the fundus of the subject eye 12 and enables fundus observation of the subject eye 12 is applicable. That is, the use of reflected light from the subject eye 12 when scanned light is scanned thereon is not limiting; a function that simply illuminates light to observe the subject eye 12 may be featured. Furthermore, illumination of light onto the subject eye 12 is not limiting. For example, a function that utilizes light generated in the subject eye 12, such as fluorescent light or the like, to observe the subject eye 12 may be featured. Thus, the concept of light for observing the subject eye 12 includes light reflected from the fundus and light generated at the fundus, and is referred to as "light from the subject eye 12".

Now, an illumination angle of luminous flux relative to the subject eye 12 at the ophthalmic imaging apparatus 10 according to the present exemplary embodiment is described.

Figure 2:
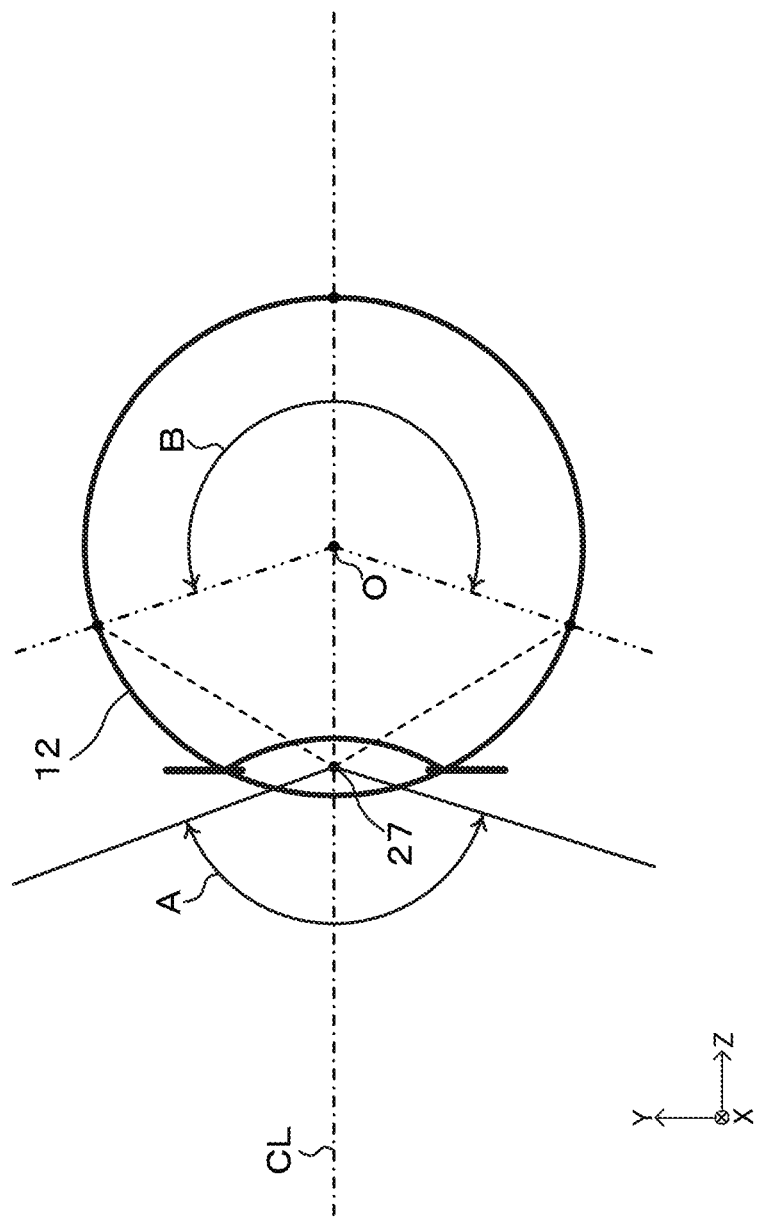
FIG. 2 is a conceptual image showing an example of an illumination angle of a subject eye at the ophthalmic imaging apparatus according to the exemplary embodiment.
Figure 3:
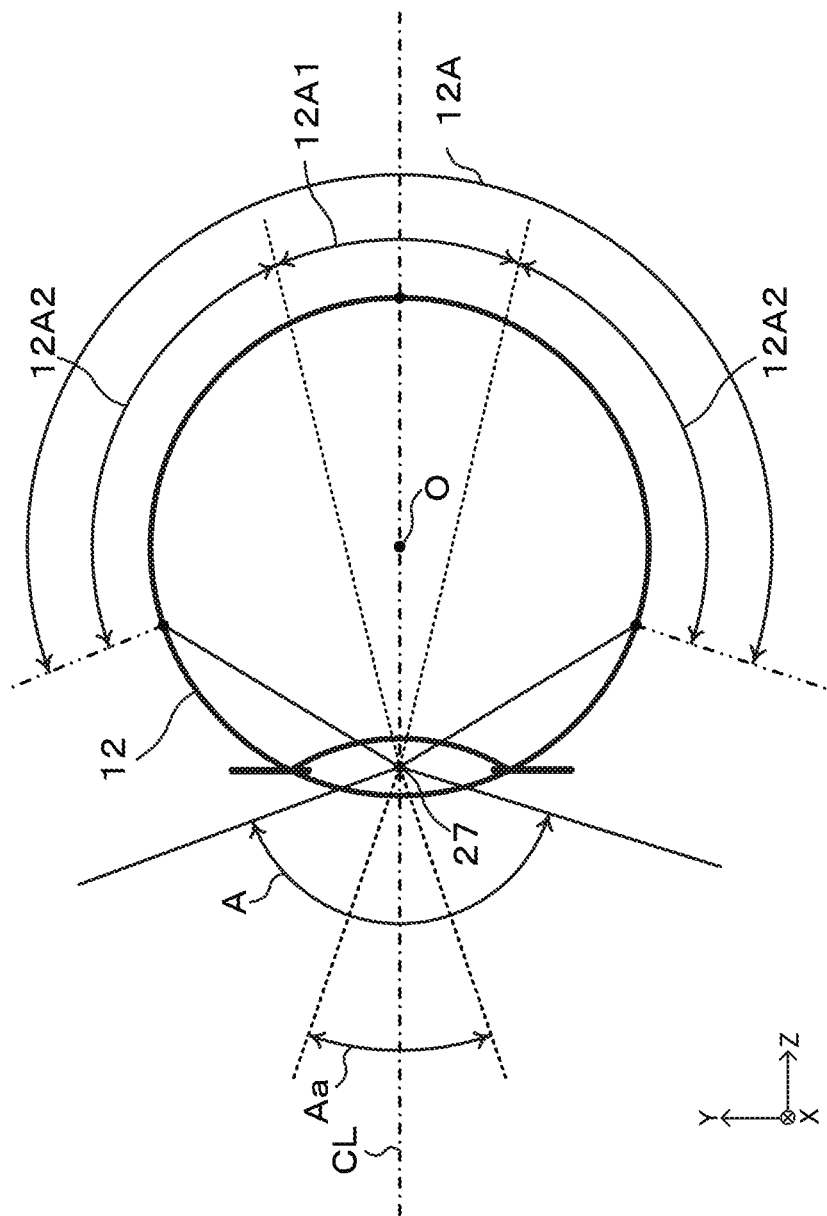
FIG. 3 is a conceptual image showing an example of an imageable region of a fundus at the ophthalmic imaging apparatus according to the exemplary embodiment.

FIG. 2 shows an example of the illumination angle of the subject eye by the ophthalmic imaging apparatus 10 according to the present exemplary embodiment. FIG. 3 shows an example of an imageable region of the fundus.

When the fundus of the subject eye 12 is being observed, a fundus region with a greater range may be observed by making a field of view (FOV) for an observer observing the fundus, which is to say a field of view of the fundus, a wider angle. In order to observe the fundus region, in the ophthalmic imaging apparatus 10 according to the present exemplary embodiment, the fundus of the subject eye 12 is scanned with the scanned light and the fundus of the subject eye 12 is imaged. Therefore, the field of view of the fundus corresponds to the illumination angle of the scanned light. That is, it is apparent that the greater the extent of light provided to the subject eye 12, the greater the fundus region that can be imaged. Light being scanned onto the fundus is illuminated toward the center of the pupil of the subject eye 12. Because of refraction in the cornea of the subject eye, illuminated light from the ophthalmic apparatus illuminates the fundus across a somewhat narrower angle inside the subject eye. FIG. 2 schematically shows illuminated light rays from the ophthalmic apparatus in states that are refracted at the center of the pupil. Thus, it is necessary to distinguish between an external illumination angle A of light illuminated from the outside by the ophthalmic apparatus and an internal illumination angle B of illuminated light inside the subject eye that is being illuminated.

The external illumination angle A is the light illumination angle from the ophthalmic imaging apparatus 10 side, that is, from outside the subject eye 12. That is, an angle across which illuminated light toward the fundus of the subject eye 12 approaches a pupil center point 27 of the subject eye 12 (that is, a central point in an elevation view of the pupil) serves as the external illumination angle A. The external illumination angle A is equal to an angle across which light reflected from the fundus is emitted from the subject eye 12 toward the ophthalmic imaging apparatus 10, through the pupil center point 27. The internal illumination angle B represents a light illumination angle across the fundus of the subject eye 12 that is illuminated by the scanned light and effectively imaged, using the eyeball center O of the subject eye 12 as a reference point. The external illumination angle A and the internal illumination angle B are in correspondence with one another. In the descriptions below, because the ophthalmic apparatus is being described, the external illumination angle A is used as an illumination angle corresponding to the field of view of the fundus. Where the internal illumination angle is also mentioned in the descriptions below, it is given for reference.

Thus, as illustrated in FIG. 3, the ophthalmic imaging apparatus 10 images inside the imageable region 12A, which is a fundus region of the subject eye 12, in accordance with the external illumination angle A. The imageable region 12A is, for example, a maximum region that can be scanned with the scanned light by the scanning device 19. The imageable region 12A is, far example, a range that provides a field of view corresponding to an external illumination angle A of about 120°, which corresponds to an internal illumination angle of around 160°.

The imageable region 12A may be broadly divided into, for example, a first imageable region 12A1 and a second imageable region 12A2. The first imageable region 12A1 is the range of a field of view according to an external illumination angle Aa, in the vicinity of a visual axis CL that passes through the pupil center point 27 and the center O of the subject eye 12. The second imageable region 12A2 is a region surrounding the first imageable region 12A1, which is the range of a peripheral field of view that is more distant from the visual axis CL. The external illumination angle Aa corresponding to the first imageable region 12A1 is, for example, about 30° (corresponding to an internal illumination angle B of around 45°), and the external illumination angle A corresponding to the second imageable region 12A2 is, for example, about 120° (corresponding to an internal illumination angle of around 160°).

The scanning device 19 includes a common optical system 28 that is equipped with the first optical scanner 22, the second optical scanner 24, a dichroic mirror 26 and the third optical scanner 29. The first optical scanner 22, the second optical scanner 24 and the dichroic mirror 26 are disposed such that an optical path length between the first optical scanner 22 and the dichroic mirror 26 matches an optical path length between the second optical scanner 24 and the dichroic mirror 26. The common optical system 28 is used in common for both the SLO light and the illuminating light. The common optical system 28 includes the third optical scanner 29. The first optical scanner 22, the second optical scanner 24 and the third optical scanner 29 are disposed at positions that are conjugate with a central portion of the pupil of the subject eye 12. Including the dichroic mirror 26 in the common optical system is conceivable because the dichroic mirror 26 is used in common by both scanners.

In the present exemplary embodiment, a polygon mirror is used as an example of the first optical scanner 22, and a mirror galvanometer is used as an example of the second optical scanner 24. It is sufficient that the first optical scanner 22 and the second optical scanner 24 are optical elements that are capable of deflecting luminous flux in predetermined directions.

Figure 4:
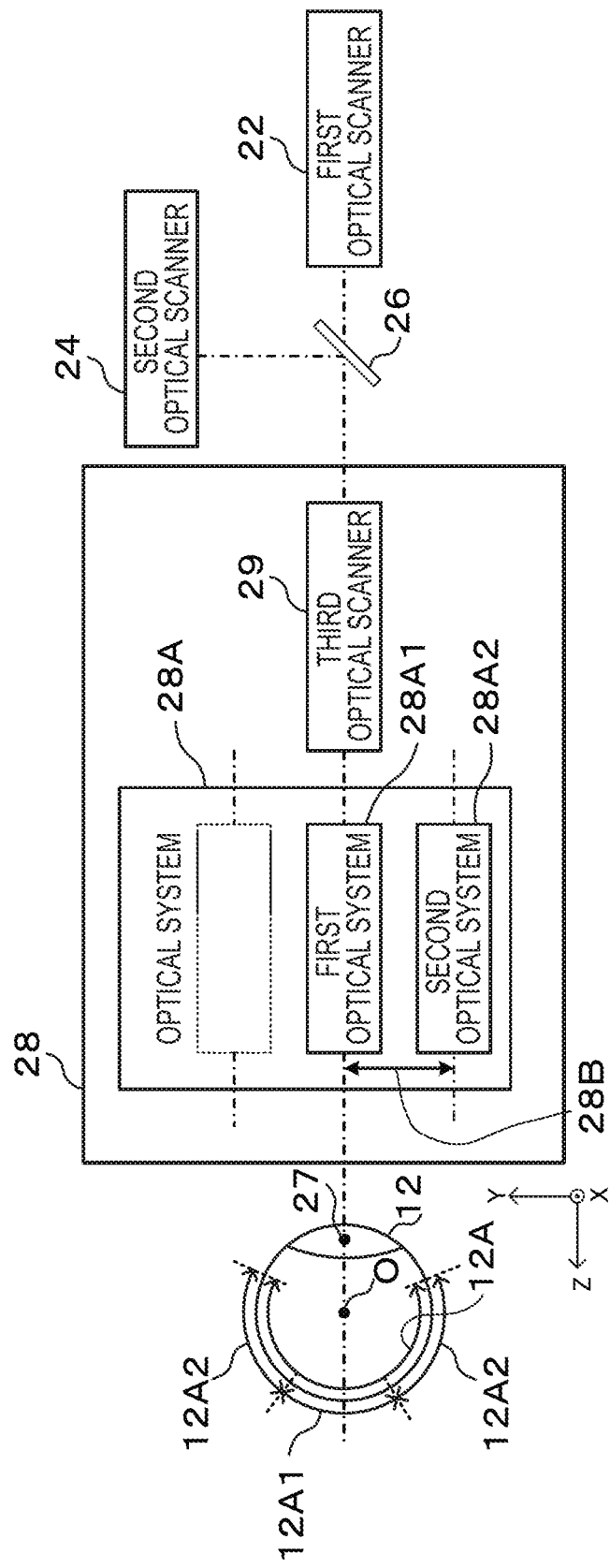
FIG. 4 is a schematic structural diagram showing an example of a scanning device included in the ophthalmic imaging apparatus according to the exemplary embodiment.

FIG. 4 shows an example of the scanning device 19 including principal structures of the common optical system 28.

As shown in FIG. 4, the common optical system 28 includes an optical system 28A and the third optical scanner 29. In the optical system 28A, a first optical system 28A1 that pertains to a field of view of a fundus central portion centered on an optical axis serves as a standard optical system operating as the common optical system 28. The optical system 28A includes a replacement mechanism 28B that is capable of switching the optical system operating as the common optical system 28 from the first optical system 28A1 to a second optical system 28A2 that pertains to a field of view of a fundus surroundings portion surrounding the fundus central portion. For example, a moving mechanism such as a rotating stage, a single-axis stage or the like may be used as the replacement mechanism 28B. That is, in accordance with operation of the replacement mechanism 28B in the present exemplary embodiment, either of the first optical system 28A1 and the second optical system 28A2 of the optical system 28A can be specified as an optical system for imaging the fundus of the subject eye 12. Details of the first optical system 28A1 and the second optical system 28A2 are described below.

The replacement mechanism 28B may be structured to be switchable by manual operation by a user. The replacement mechanism 28B may be equipped with a driving device, which is not shown in the drawings, and the driving device that is not shown in the drawings may drive in response to switching commands from the control device 16 so as to switch to the first optical system 28A1 or the second optical system 28A2.

The first optical scanner 22 sends the SLO light from the SLO unit 18 to the dichroic mirror 26. The first optical scanner 22 scans the SLO light in the Y direction. This scanning of the SLO light in the Y direction is implemented by operation of a light-deflecting element such as a polygon mirror or the like. The dichroic mirror 26 transmits the SLO light sent from the first optical scanner 22 and guides the SLO light to the common optical system 28. In the common optical system 28, the SLO light is emitted from the third optical scanner 29 into the optical system 28A (the first optical system 28A1 or the second optical system 28A2). The third optical scanner 29 scans the SLO light in the X direction. The scanning of the SLO light in the X direction is implemented by operation of a light-deflecting element such as a mirror galvanometer or the like.

In the common optical system 28, the SLO light from the third optical scanner 29 passes through the optical system 28A, and is incident on the pupil of the subject eye 12. The SLO light is reflected by the imageable region 12A. The reflected SLO light follows the same optical path as the SLO light in the opposite direction and reaches the SLO unit 18.

The second optical scanner 24 sends the measurement light from the OCT unit 20 to the dichroic mirror 26. The second optical scanner 24 scans the measurement light in the Y direction. This scanning of the measurement light in the Y direction is implemented by operation of a light-deflecting element such as a mirror galvanometer or the like. The dichroic mirror 26 reflects the measurement light sent from the second optical scanner 24 and guides the measurement light to the common optical system 28. In the common optical system 28, the measurement light is emitted from the third optical scanner 29 into the optical system 28A (the first optical system 28A1 or the second optical system 28A2). The third optical scanner 29 scans the measurement light in the X direction.

In the common optical system 28, the measurement light from the third optical scanner 29 passes through the optical system 28A, and is incident on the pupil of the subject eye 12. The measurement light is incident on the imageable region 12A and is scattered in directions different from the tissue thickness direction of the imageable region 12A or reflected. Reflected measurement light that is obtained as a result follows the same optical path as the measurement light in the opposite direction and reaches the OCT unit 20.

Figure 5:
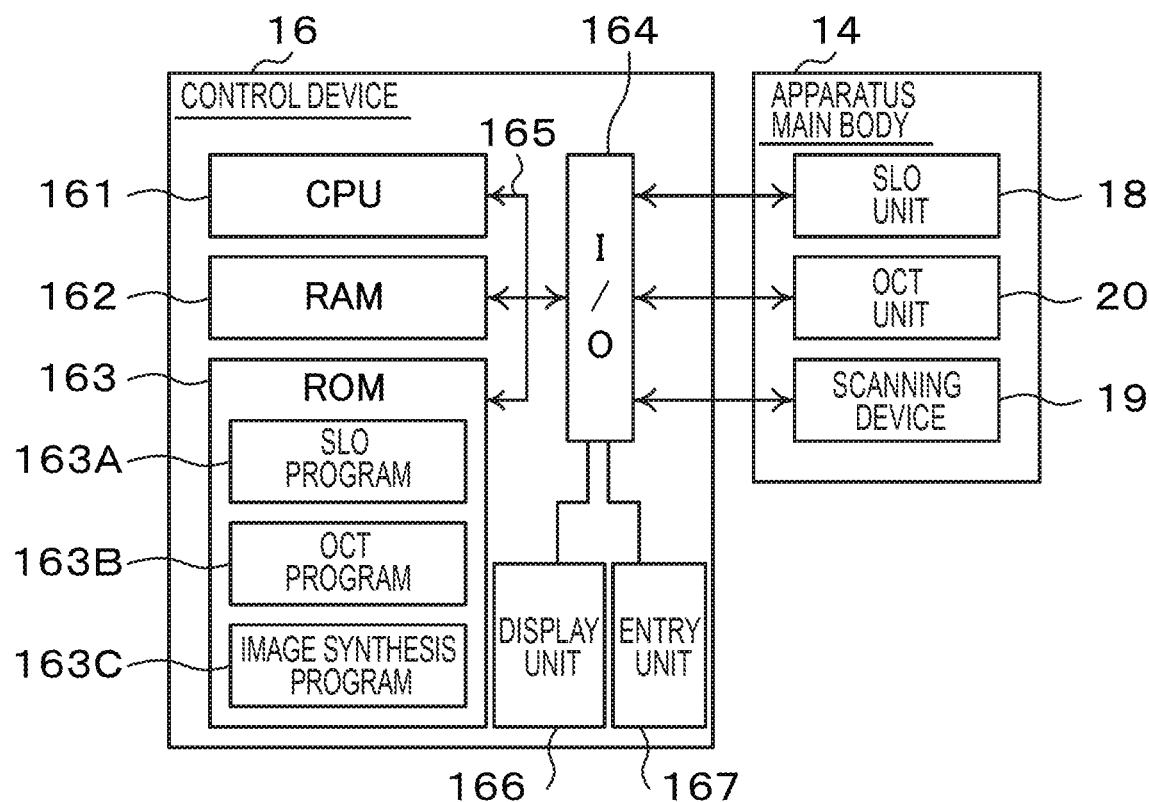
FIG. 5 is a block diagram showing an example of structure of a control device included in the ophthalmic imaging apparatus according to the exemplary embodiment, which control device is realized by a computer.

FIG. 5 shows an example of structure of the control device 16, which is realized by a computer.

As shown in FIG. 5, the control device 16 is realized by a computer including a central processing unit (CPU) 161, random access memory (RAM) 162 and read-only memory (ROM) 163. The ROM 163 contains a control program for executing various functions for forming images of the fundus of the subject eye 12. In the present exemplary embodiment, as an example, the control program includes an SLO program 163A, an OCT program 163B and an image synthesis program 163C. The control device 16 is provided with an input/output (I/O) interface 164. The CPU 161, RAM 162, ROM 163 and I/O interface 164 are connected via a bus 165 to be capable of exchanging commands and data. A display unit 166 such as a display that displays images or the like and an entry unit such as a keyboard and mouse or the like, at which instructions to the control device 16 are entered, are also connected to the I/O interface 164. The SLO unit 18, OCT unit 20 and scanning device 19 are connected to the I/O interface 164.

The SLO program 163A describes a process for implementing the SLO imaging system function. The scanning device 19 including the SLO unit 18 and the first optical scanner 22 is controlled by execution of this process. That is, the control device 16 reads the SLO program 163A from the ROM 163 and loads the SLO program 163A into the RAM 162, and the SLO program 163A loaded into the RAM 162 is executed by the CPU 161. Thus, the control device 16 operates as a control section of the SLO imaging system function. Thus, the control device 16 controls the SLO unit 18 and the scanning device 19 and generates a two-dimensional image 12G representing the imageable region 12A. The two-dimensional image 12G is a flat image representing a planar view of the imageable region 12A.

The OCT program 163B describes a process for implementing the OCT imaging system function. The scanning device 19 including the OCT unit 20 and the second optical scanner 24 is controlled by execution of this process. That is, the control device 16 reads the OCT program 163B from the ROM 163 and loads the OCT program 163B into the RAM 162, and the OCT program 163B loaded into the RAM 162 is executed by the CPU 161. Thus, the control device 16 operates as a control section of the OCT imaging system function. Thus, the control device 16 controls the OCT unit 20 and the scanning device 19 and generates tomography images of the fundus of the subject eye 12, that is, tomographic images of the interior of the imageable region 12A.

The image synthesis program 163C describes a process for implementing a function that synthesizes captured images of the first imageable region 12A1 and second imageable region 12A2 of the subject eye 12 (see FIG. 3). By the execution of this process, the images are synthesized and a fundus image is formed. That is, the control device 16 reads the image synthesis program 163C from the ROM 163 and loads the image synthesis program 163C into the RAM 162, and the image synthesis program 163C loaded into the RAM 162 is executed by the CPU 161. Thus, the control device 16 operates as a control section that synthesizes images obtained by the SLO imaging system function and the OCT imaging system function.

Figure 6:
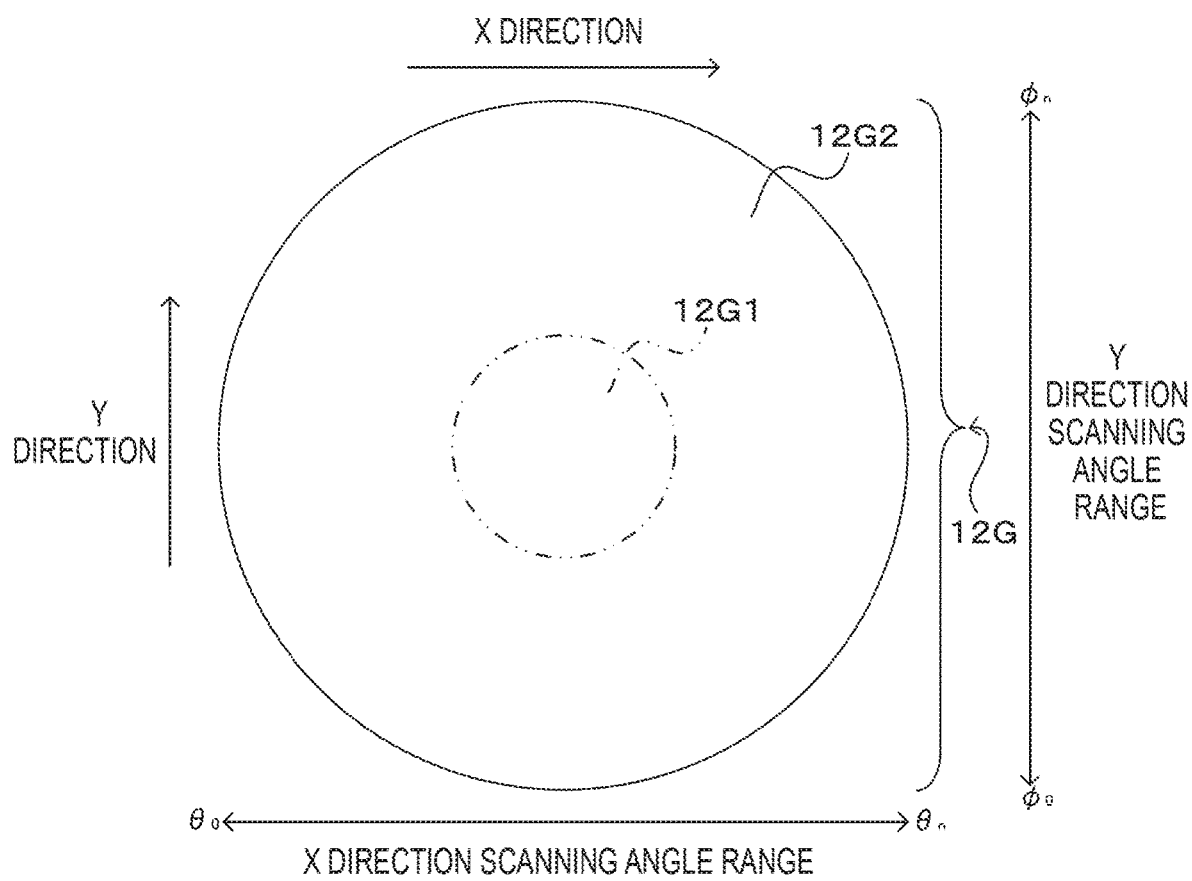
FIG. 6 is a conceptual image showing an example of a two-dimensional image acquired by the ophthalmic imaging apparatus according to the exemplary embodiment.

FIG. 6 shows an example of the two-dimensional image 12G representing the imageable region 12A that is generated by the control device 16.

As shown in FIG. 6, an X direction scanning angle range is the range of the scanning angle of the scanned light in the X direction. In FIG. 6, as an example, the X direction scanning angle range is a range from θ0° at least to θn° at most. A Y direction scanning angle range is the scanning angle of the scanned light in the Y direction. In FIG. 6, as an example, the Y direction scanning angle range is a range from φ0°) at least to φn° at most.

As shown in FIG. 6, the two-dimensional image 12G is broadly divided into a circular first fundus image region 12G1 that corresponds with the first imageable region 12A1 (see FIG. 3) and an annular second fundus image region 12G2 that corresponds with the second imageable region 12A2 (see FIG. 3). However, it is not easy to obtain images of the first fundus image region 12G1 and the second fundus image region 12G2 with high accuracy from the same scan.

More specifically, the first optical system 28A1 that pertains to the field of view of the fundus central portion centered on the optical axis serves as the standard for the optical system 28A, and the first optical system 28A1 can be replaced with the second optical system 28A2 that pertains to the annular field of view of the fundus surroundings portion surrounding the fundus central portion (see FIG. 4). The first optical system 28A1 images the first imageable region 12A1 (see FIG. 3), which is the fundus central portion of the subject eye 12. The second optical system 28A2 images the second imageable region 12A2 (see FIG. 3), which is the fundus surroundings portion of the subject eye 12.

Figure 7A:
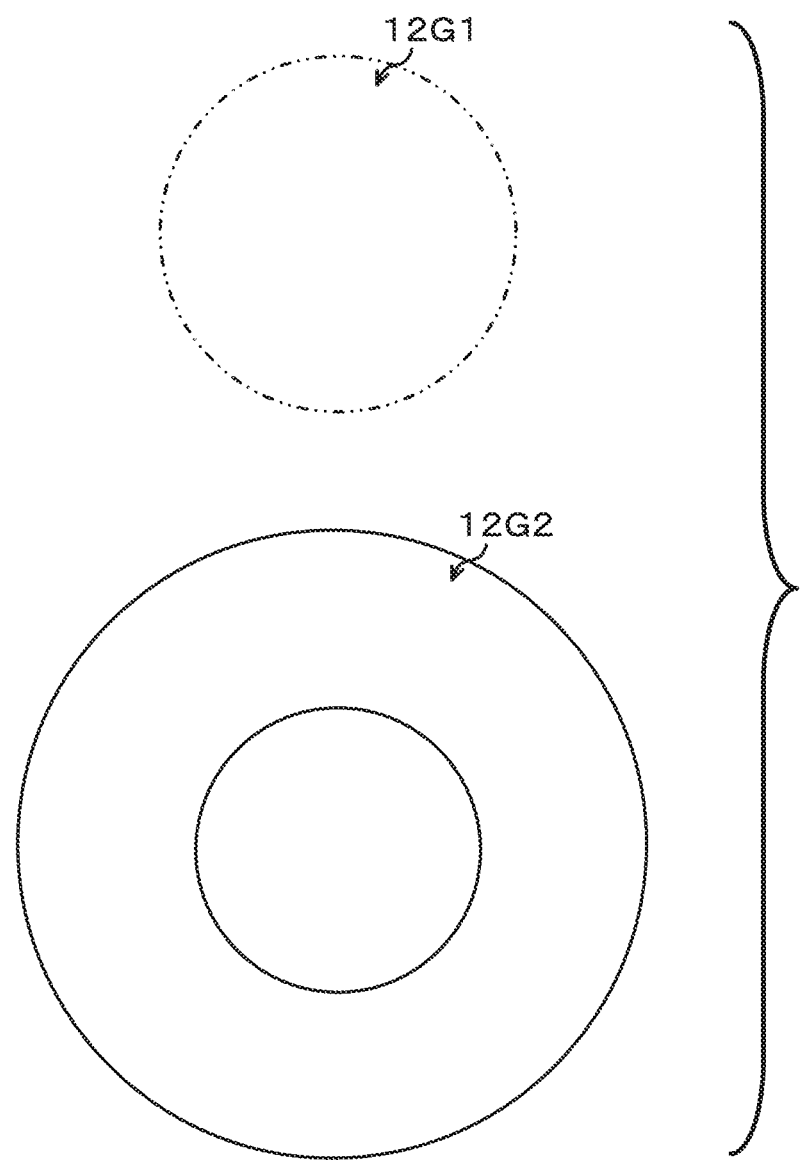
FIG. 7A is a conceptual image schematically showing an example of a two-dimensional image generated by the control device according to the exemplary embodiment, which is a two-dimensional image in which a first fundus image region and a second fundus image region are spliced together.
Figure 7B:
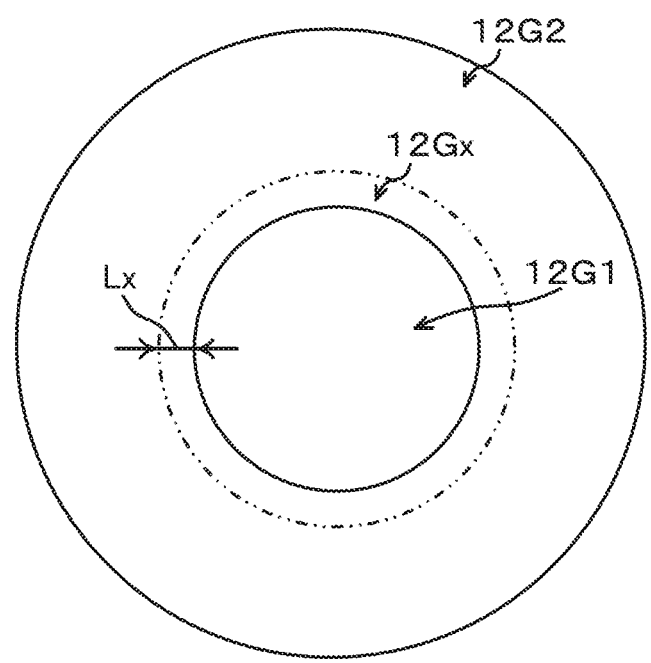
FIG. 7B is a conceptual image schematically showing an example of a two-dimensional image generated by the control device according to the exemplary embodiment, which is a two-dimensional image in which portions of the first fundus image region and the second fundus image region are superposed.

FIG. 7A and FIG. 7B schematically show examples of the two-dimensional image 12G generated by the control device 16. FIG. 7A shows a case in which the small, circular first fundus image region 12G1 and the annular second fundus image region 12G2 surrounding the first fundus image region 12G1 are spliced together to form the two-dimensional image 12G. FIG. 7B shows a case in which portions of the first fundus image region 12G1 and the second fundus image region 12G2 (i.e., an annular strip with a width Lx in the radial direction) are superposed to form the two-dimensional image 12G.

As shown in FIG. 7A, the control device 16 generates the two-dimensional image 12G corresponding to the imageable region 12A of the fundus by splicing the first fundus image region 12G1 captured by the first optical system 28A1 with the second fundus image region 12G2 captured by the second optical system 28A2. Alternatively, as shown in FIG. 7B, the control device 16 generates the two-dimensional image 12G corresponding to the imageable region 12A of the fundus by superposing portions of the first fundus image region 12G1 captured by the first optical system 28A1 and the second fundus image region 12G2 captured by the second optical system 28A2. When portions of the first fundus image region 12G1 and the second fundus image region 12G2 are to be superposed, the first fundus image region 12G1 may be synthesized with the second fundus image region 12G2 to generate a superposed image 12Gx, or either one of the first fundus image region 12G1 and second fundus image region 12G2 may be utilized for the superposed image 12Gx. Further, when portions of the first fundus image region 12G1 and second fundus image region 12G2 are to be superposed, the size of the superposed image 12Gx may be entered by a user.

The synthesis processing that synthesizes the first fundus image region 12G1 with the second fundus image region 12G2 may be, for example, processing that uses 3D data or scan data obtained from the OCT units 20 to generate a three-dimensional image, sectional images and a surface image, and that executes segmentation processing. The fundus image may also be generated by using data obtained from the respective SLO units 14.

When synthesizing the images, it is sufficient to execute, for example, image processing such as rotation, magnification/reduction and the like of the images such that patterns of blood vessels in the images are superposed. The synthesized image may provide a wide-angle image as if a wide-angle image exceeding 100° were captured by ophthalmic equipment for capturing wide-angle images. It will be clear that the image processing that synthesizes the images is not limited to the techniques mentioned above and that widely known techniques may be employed.

Now, the optical system 28A included in the common optical system 28 is described in detail. With the ophthalmic imaging apparatus 10, it is necessary to image a wide range in the imageable region 12A of the fundus of the subject eye 12. However, it would not be easy to make the external illumination angle of the subject eye 12 ultrawide and to obtain a wider field of view with the ophthalmic imaging apparatus 10 employing only refracting lenses. This is because it is necessary to address a number of problems, such as conserving a working distance WD between the subject eye 12 and an optical system surface that is closest to the subject eye 12, improving aberration characteristics in order to obtain high resolution images, suppressing flares and ghosts, keeping down the size and weight of the apparatus main body, and moderating fabrication difficulty and costs. These problems tend to come into conflict in accordance with attempts to obtain a wider field of view. For example, choosing either a wider field of view or a smaller optical system for the ophthalmic imaging apparatus 10 is unavoidable.

Accordingly, the present inventors have devised the ophthalmic imaging apparatus 10 according to the present exemplary embodiment with consideration for the fact that many fundus observations are observations of fundus central portions and the fact that a catadioptric optical system, which combines reflective surfaces with refracting lenses, may suppress chromatic aberration in an optical system as a whole and enable a reduction in size of the optical system. That is, in the present exemplary embodiment, the first optical system 28A1 that is pertinent to observation of a fundus central portion is structured by two optical units. Of the two optical units, the optical unit at the side at which the subject eye 12 is disposed can be replaced with a different optical unit constituted by a catadioptric optical system. The second optical system 28A2 that enables observation of periphery portions requiring wider angles is structured as a separate optical system resulting from this replacement. In other words, in the ophthalmic imaging apparatus 10 that is provided, the optical unit at the side at which the subject eye is disposed may be switched between the first optical system 28A1 for a central field of view and the second optical system 28A2 for a peripheral field of view, and the other optical unit may be employed as a common optical unit. In the descriptions below, descriptions are given centering on the fundus imaging apparatus that images the fundus of the subject eye 12. However, the apparatus is not limited to observing the fundus but, by appropriate selection of positional relationships with the subject eye 12 in accordance with the optical configuration mentioned above, is also effective when the observed field of view is switched to a cornea portion of the subject eye or the like.

Figure 8:
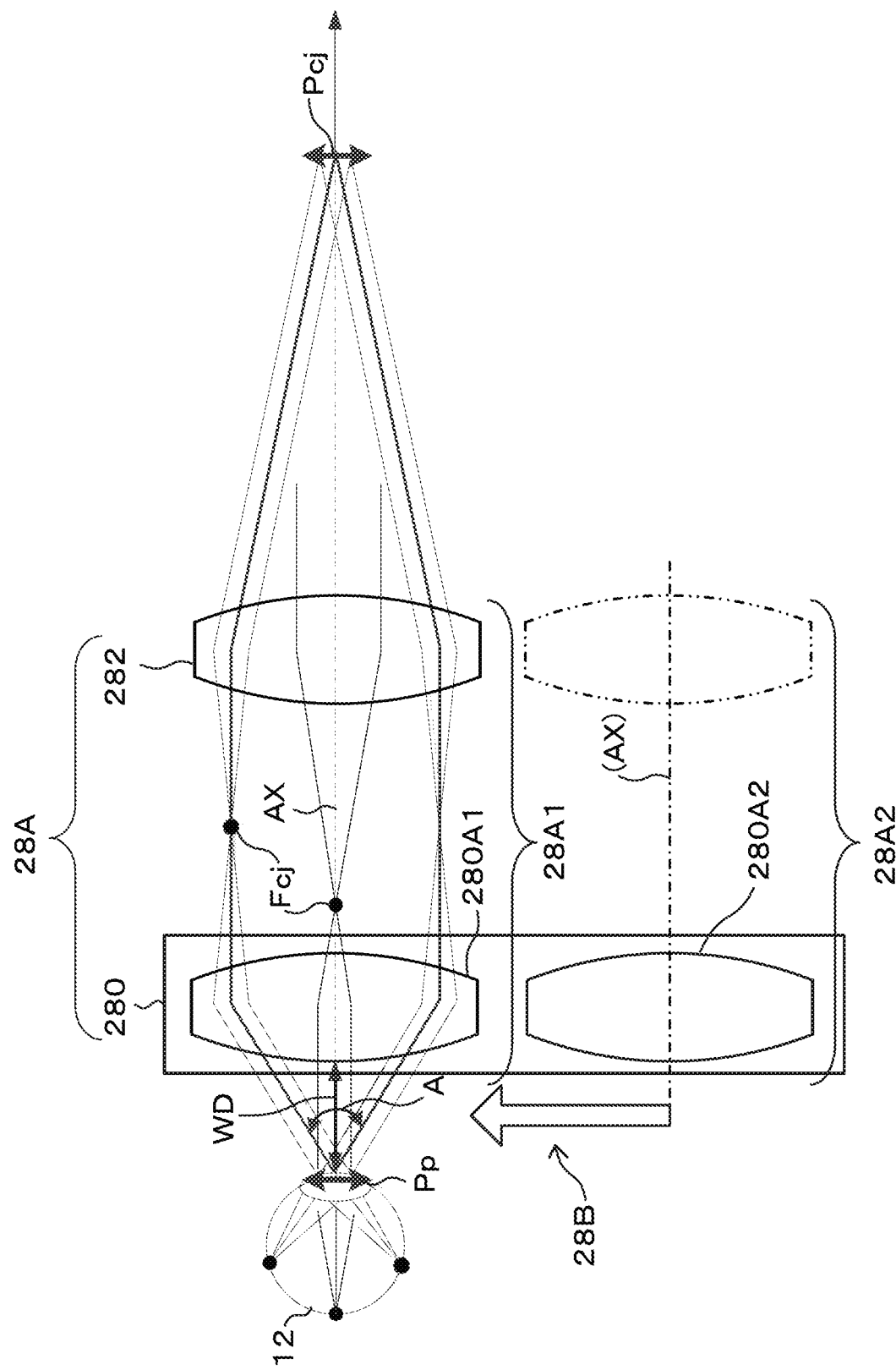
FIG. 8 is a schematic diagram of an optical system of a common optical system included in the ophthalmic imaging apparatus according to the exemplary embodiment.

FIG. 8 schematically shows the optical system 28A of the common optical system 28, which is capable of realizing a wider angle. As shown in FIG. 8, the optical system 28A includes an optical unit 280 and a rear optical unit (common optical unit) 282 in this order from the side at which the subject eye 12 is disposed.

The optical system for observing the fundus central portion of the subject eye, that is, the first optical system 28A1 that is pertinent to a field of view of the fundus central portion centered on an optical axis AX, is structured by a first optical unit 280A1 and the common optical unit 282, which serves as a rear optical unit. The optical system for observing the fundus surroundings portion of the subject eye, that is, the second optical system 28A2 that is pertinent to a field of view of the fundus surroundings portion surrounding the fundus central portion, includes a second optical unit 280A2, which is a catadioptric optical unit, and the common optical unit 282 serving as the rear optical unit. In the present exemplary embodiment, when the first optical system 28A1 is being replaced with the second optical system 28A2, the first optical unit 280A1 is replaced with the second optical unit 280A2 by the replacement mechanism 28B.

The second optical unit 280A2 is formed as a catadioptric optical unit. According to a catadioptric optical system structured by combining reflective surfaces with refracting lenses, chromatic aberration in the optical system as a whole may be suppressed and a reduction in size of the optical system may be enabled. Therefore, in the present exemplary embodiment, splitting of optical flux incident on a reflective surface and reflected optical flux is possible, and observation of larger portions of the fundus surroundings is enabled. In more detail, the catadioptric optical unit that serves as the second optical system 28A2 pertinent to the field of view of the fundus surroundings portion surrounding the fundus central portion employs a reflective surface including an aperture portion centered on the optical axis, for example, a reflecting mirror with an annular effective reflection region, and a refracting lens to form an annular field of view. Consequently, an optical system with satisfactory aberration characteristics for an image with an ultrawide angle, and that suppresses flares and ghosts even while sizes and numbers of lenses are reduced, is realized.

However, because the second optical system 28A2 has an annular field of view, observation over the whole of the fundus interior is difficult. Accordingly, observation over the whole of the fundus interior is enabled by forming a combination with the first optical unit 280A1, which is a small, refractive, observing optical system with a small field of view, and switching the first optical unit 280A1 with the second optical unit 280A2.

In the ophthalmic imaging apparatus 10 according to the present exemplary embodiment, substituting an entire optical system including the SLO unit 18 and the OCT unit 20 inevitably increases the size and complexity of the apparatus. Therefore, the first optical system 28A1 and the second optical system 28A2 of the common optical system 28 are configured so as to satisfy the conditions in the following expression (1), as a result of which an optical system at a light emission side of a first pupil conjugate Pcj position may be used in common with both.

$$0.2<\beta1\cdot(1-M2)/\beta2\cdot(1-M1)<1.0 \qquad (1)$$

In this expression, β1 represents an imaging magnification of the first optical system 28A1 between a pupil Pp position of the subject eye 12 and the pupil conjugate Pcj position, M1 represents a distortion factor by the first optical system 28A1 of the maximum field of view at a fundus conjugate Fcj when an aplanatic ideal lens is included at the pupil conjugate Pcj position, β2 represents an imaging magnification of the second optical system 28A2 between the pupil Pp position of the subject eye and the pupil conjugate Pcj position, and M2 represents a distortion factor by the second optical system 28A2 of the maximum field of view at the fundus conjugate Fcj when the aplanatic ideal lens is included at the pupil conjugate Pcj position. The aplanatic ideal lens is suitably included for convenience of description, but included elements are not limited to the aplanatic ideal lens.

Rapid scanning observations may be enabled by configuring the first optical system 28A1 and second optical system 28A2 of the common optical system 28 so as to satisfy the conditions in the following expressions (2) and (3).

$$2<\theta1/(1-M1)<13 \qquad (2)$$

$$9<\theta2/(1-M2)<17 \qquad (3)$$

In both the first optical system 28A1 and the second optical system 28A2, optical elements with refractivity are arranged along the single optical axis AX. Therefore, a level of difficulty of adjustment of each optical system may be lowered compared to a situation in which optical elements with refractivity are not disposed on a single optical axis. Note that deflecting the optical axis with deflecting mirrors or the like does not increase the difficulty of adjustment.

If the distance from the pupil Pp position of the subject eye 12 to the pupil conjugate Pcj position changes greatly with the substitution of the optical unit, it is necessary to move the position of the subject eye 12 or move the optical system of the apparatus, which lengthens a time required for observation of the whole of the fundus interior. That is, a time interval of switching from one to the other of an image of the fundus central portion and an image of the fundus surroundings portion is greater, as a result of which the time required for observation of the whole of the fundus interior increases. Thus, the ophthalmic imaging apparatus 10 that is capable of observing the whole of the fundus interior falls into circumstances that are not preferable.

Accordingly, variations in the distance from the pupil Pp position of the subject eye 12 to the pupil conjugate Pcj position with substitutions of the optical units may be suppressed by suppressing a difference between the distance in the first optical system 28A from the pupil Pp position of the subject eye 12 to the pupil conjugate Pcj position1 and the distance in the second optical system 28A2 from the pupil Pp position of the subject eye 12 to the pupil conjugate Pcj position. More specifically, it is sufficient to configure the first optical system 28A1 and the second optical system 28A2 of the common optical system 28 so as to satisfy the conditions in the following expression (4).

$$0.8<L1/L2<1.2 \qquad (4)$$

In this expression, L1 represents the distance from the pupil Pp position of the subject eye 12 to the pupil conjugate Pcj position in the first optical system 28A1, and L2 represents the distance from the pupil Pp position of the subject eye 12 to the pupil conjugate Pcj position in the second optical system.

Comatic aberration of the pupil between the pupil Pp of the subject eye 12 and the pupil conjugate Pcj causes a difference in the luminous flux angle of a fundus image at the pupil conjugate Pcj image position, which leads to a change in resolving power at the fundus position. In order to correct this comatic aberration of the pupil, it is preferable to dispose a lens group with a positive refractivity overall between the fundus conjugate Fcj position that is conjugate with the fundus of the subject eye 12 and the pupil conjugate Pcj position, and to configure a face with a negative refractivity at at least one surface in this lens group.

The common optical system 28 including the first optical system 28A1 and second optical system 28A2 that are configured in this manner may be switched by the switching mechanism 28B from imaging of a circular field of view to an ultrawide-angle annular field of view. This structure is easily applied to eye examinations in ophthalmology, most of which involve observations of the fundus central portion, and may smoothly transfer to observations of a large region surrounding the fundus central portion.

Eye examinations in ophthalmology are often required after observation of the fundus central portion. Therefore, higher resolving power is required in observations during examinations. This requirement may be satisfied by configuring the first optical system 28A1 and second optical system 28A2 of the common optical system 28 so as to satisfy the conditions in the following expression (5). In this case, it is preferable to dispose an aperture for satisfying these conditions in the vicinity of a position that is conjugate with the pupil surface.

$$1.0 \le H1/H2 < 5.0 \qquad (5)$$

In this expression, H1 represents an effective aperture diameter of the first optical system 28A1 in the plane of the pupil Pp position at the subject eye 12, and H2 represents an effective aperture diameter of the second optical system 28A2 in the plane of the pupil Pp position at the subject eye 12. It is preferable if the upper limit is smaller than 3.0.

It is preferable to automatically detect which optical unit is being used—the circular field of view imaging system (standard) based on the first optical system 28A1 or the annular field of view optical system (ultrawide angle) based on the second optical system 28A2—and, depending on the detected optical unit, to automatically specify a scanning angle of the second optical scanner 29 disposed in the vicinity of the pupil conjugate Pcj position, on/off control of illumination light in accordance with angles, the diameter of an aperture disposed in the vicinity of the conjugate position of the pupil surface, and the like.

It is generally not easy to increase the working distance WD between the subject eye 12 and the optical system of the optical system 28. However, in the present exemplary embodiment, reflective surfaces and lenses are utilized, and the reflective surfaces have annular effective reflection regions with transmission apertures at the centers of the reflective surfaces. Because the present exemplary embodiment includes an annular field of view, images of the ultrawide-angle region have satisfactory aberration characteristics, and an optical system with few occurrences of flares and ghosts, small size, and a small number of structural lenses may be realized.

Now, the second optical system 28A2 is described in detail. The second optical system 28A2 includes two optical units. The optical unit 280A2 at the side of the second optical system 28A2 at which the subject eye is disposed is a catadioptric optical unit. In the order in which light is incident in the optical unit 280A2 from the side at which the pupil Pp of the subject eye 12 is disposed, spreading of luminous flux of the light from the subject eye 12 is suppressed by a first refracting face, at which a concave surface faces to the side at which the subject eye is disposed, and the light from the subject eye 12 is reflected and converged in directions toward the subject eye 12 by a first reflection surface including a central aperture centered on the optical axis. Then, at a second reflection surface, the light is reflected to the opposite direction from the direction toward the subject eye 12, and is transmitted through the aperture of the first reflection surface that is centered on the optical axis. The succeeding optical unit 282 forms light from this catadioptric optical unit into a pupil conjugate Pcj image that is conjugate with the pupil Pp position of the subject eye 12. The succeeding optical unit 282 is the same as the second optical unit 282 of the first optical system 28A1. A satisfactory working distance WD may be assured and the first reflection surface may be reduced in size by the concave first refraction face, and luminous flux splitting is enabled by the light being transmitted through the aperture portions centered on the optical axis in the convex second reflection surface and the concave first reflection surface. In addition, the optical system may be reduced in size, which is advantageous.

Back-face reflective surfaces that are integral structures formed at the surfaces at both sides of a medium with a refractive index greater than 1 are employed as the first reflection surface including an aperture centered on the optical axis and the second reflection surface including an aperture centered on the optical axis. Thus, it is possible to realize both assurance of a longer working distance WD and formation with smaller reflecting mirrors.

First Practical Example

Figure 9:
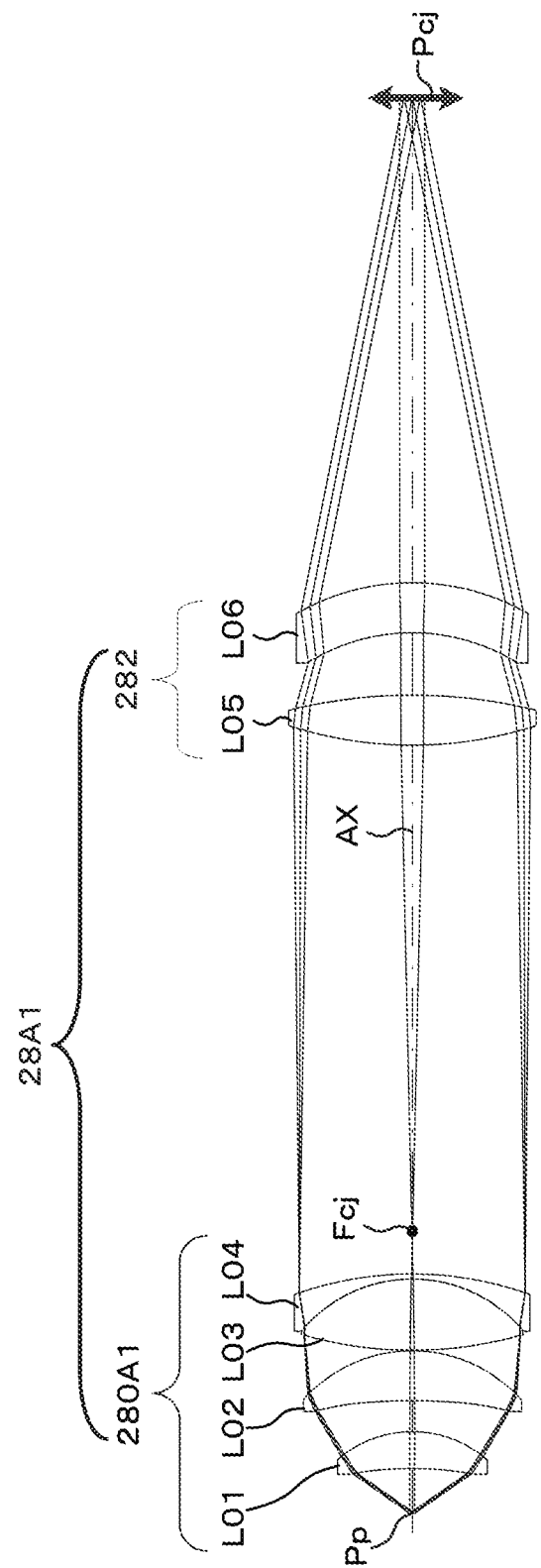
FIG. 9 is a structural diagram showing an example of a lens configuration of a first optical system according to practical example 1-1.

FIG. 9 shows a lens configuration of the optical system 28A of the ophthalmic imaging apparatus 10 according to a first practical example, which is illustrated as practical example 1-1.

The first optical system 28A1 includes the first optical unit 280A1. In the first optical unit 280A1, a positive meniscus lens L01, a positive meniscus lens L02 with an aspherical shape, a convex lens L03 and a negative meniscus lens L04 are arrayed in a lens group in this order from the side thereof at which the pupil Pp of the subject eye 12 is disposed. A concave surface of the positive meniscus lens L01 faces to the side at which the pupil Pp is disposed. A concave surface of the negative meniscus lens L02 faces to the side at which the pupil surface D is disposed. The negative meniscus lens L04 is mated with the convex lens L03 at the side of the negative meniscus lens L04 at which the pupil surface D is disposed. The first optical system 28A1 also includes the common optical unit 282 at the light emission side of the first optical unit 280A1. In the common optical unit 282, a convex lens L05 and a negative meniscus lens L06 are arrayed in this order from the side thereof at which the pupil Pp of the subject eye 12 is disposed. A concave surface of the negative meniscus lens L06 faces to the side at which the pupil surface D is disposed.

All of the optical elements constituting the first optical system 28A1, which is to say the optical elements included in the first optical unit 280A1 (the lenses L01, L02, L03 and L04) and the optical elements included in the common optical unit 282 (the lenses L05 and L06), are arranged along a single optical axis AX.

The aspherical surfaces are represented by the following expression (6), in which a height in a direction perpendicular to the optical axis is represented by r, a distance along the optical axis from a plane tangential to a vertex of the spherical surface to a position of the aspherical surface at height r (a sag quantity) is represented by z, the reciprocal of a vertex curvature radius is represented by c, a conic coefficient is represented by k, and nth-order aspherical surface coefficients are represented by A, B, C, D and E.

$$z=(c \cdot r^2)/[1+\{1-(1+k) \cdot r^2 \cdot c^2\}^{1/2}]+A \cdot r^4+B \cdot r^6+C \cdot r^8+D \cdot r^{10}+E \cdot r^{12} \qquad (6)$$

The following Table 1 shows values of elements of the first optical system 28A1 according to the first practical example (practical example 1-1).

Table 1 represents a situation in which the effective field of view (the total illumination angle A from the pupil) is 0°-110° (a first surface incidence angle of 0°-55°) and the working distance WD is 18 mm. The overall length (a distance L2 from the pupil Pp position of the subject eye 12 to the pupil conjugate Pcj position) is 565.25 mm, and the pupil imaging magnification β1 from the pupil Pp position to the pupil conjugate Pcj position is 4.88×. The distortion factor M1 (the distortion factor of the maximum field of view at the fundus conjugate Fcj when an aplanatic ideal lens is included at the pupil conjugate Pcj position) is 0.300.

TABLE 1

| Surface Number | Lens Number | Radius of curvature (mm) | Surface separation (mm) | Refractive index Nd, dispersion Vd | Effective radius (mm) |
|---|---|---|---|---|---|
| Subject eye | | ∞ | ∞ | | |
| 1 (pupil surface) | D | ∞ | 18.00000 | | 1.00 |
| 2 | L01 | −133.50541 | 14.67463 | 1.75500, 52.3 | 23.68 |
| 3 | | −45.02553 | 12.32309 | | 28.26 |
| 4 (aspherical surface) | L02 | −305.77937 | 20.00000 | 1.75500, 52.3 | 38.79 |
| 5 | | −57.75451 | 0.20000 | | 41.59 |
| 6 | L03 | 157.95243 | 28.46213 | 1.49782, 82.6 | 43.11 |
| 7 | L04 | −57.11258 | 2.00000 | 1.80809, 22.8 | 42.95 |
| 8 | | −138.00180 | 211.21082 | | 44.95 |
| 9 | L05 (common) | 158.55076 | 20.00000 | 1.49782, 82.6 | 47.22 |
| 10 | | −204.58045 | 24.91431 | | 46.51 |
| 11 | L06 (common) | −78.78320 | 20.00000 | 1.80809, 22.8 | 41.40 |
| 12 Pupil conjugate | | −92.55391 | 193.46853 | | 44.21 |

The aspherical surface coefficients representing the aspherical surface of surface 4 at lens L02 are as follows.

A=−0.115291E−05
B=+0.363779E−09
C=−0.562953E−13

Figure 10:
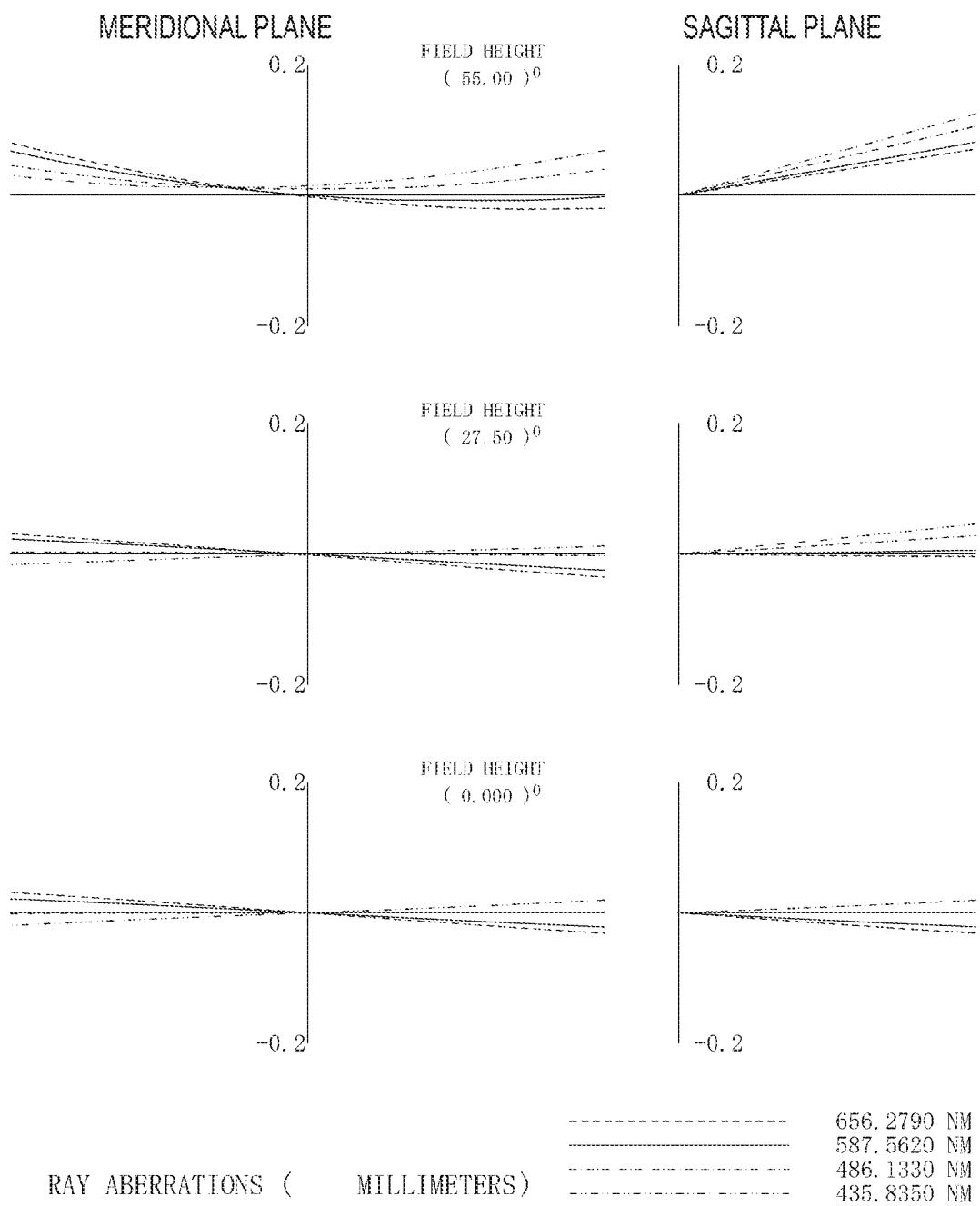
FIG. 10 is a lateral aberration diagram of the first optical system according to practical example 1-1.

FIG. 10 shows lateral aberration diagrams of the first optical system 28A1 configured in accordance with the elements in Table 2 (practical example 1-1).

In the aberration diagrams shown in FIG. 10, the vertical axis represents image height. The solid line represents a central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 10, in the first optical system 28A1 according to the first practical example, variations in aberration for lights in the visible wavelength region are suppressed and are excellently corrected. Although not shown in the drawings, it can be verified that various other aberrations such as spherical aberration, astigmatism, distortion aberration and the like are also excellently corrected.

Figure 11:
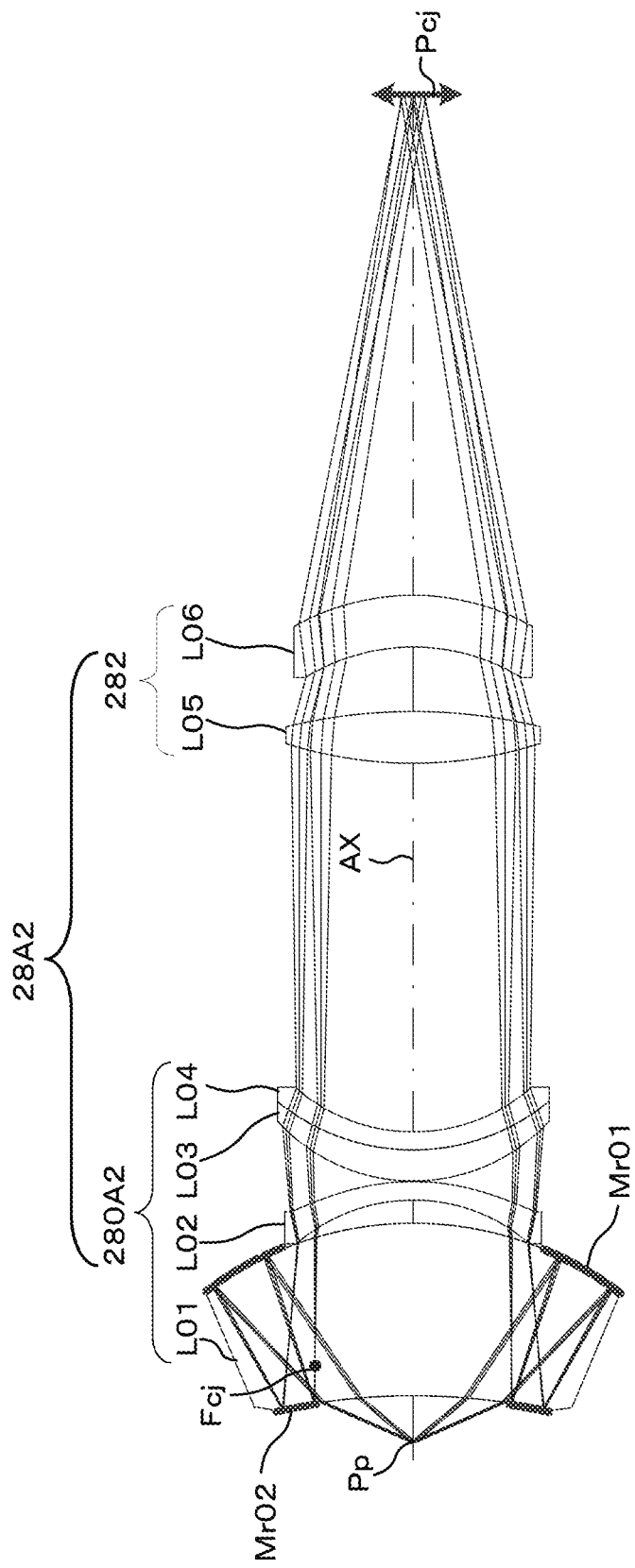
FIG. 11 is a structural diagram showing an example of a lens configuration of a second optical system according to practical example 1-2.

FIG. 11 shows a lens configuration of the second optical system 28A2 of the ophthalmic imaging apparatus 10 according to the first practical example, which is illustrated as practical example 1-2.

The second optical system 28A2 includes the second optical unit 280A2. In the second optical unit 280A2, a positive meniscus lens L01, a negative meniscus lens L02 including an aspherical surface shape, a positive meniscus lens L03 and a negative meniscus lens L04 are arrayed in a lens group in this order from the side thereof at which the pupil Pp of the subject eye 12 is disposed. A concave surface of the positive meniscus lens L01 faces to the side at which the pupil surface D is disposed. A concave surface of the negative meniscus lens L02 faces to the side at which the pupil surface D is disposed. A convex surface of the positive meniscus lens L03 faces to the side at which the pupil surface D is disposed. The negative meniscus lens L04 is mated with the positive meniscus lens L03. An optical system employed at the light emission side of the second optical unit 280A2 is used in common with the common optical unit 282 shown in FIG. 9.

The same as in the first optical system 28A1, all of the optical elements constituting the second optical system 28A2, which is to say the optical elements included in the second optical unit 280A2 (the lenses L01, L02, L03 and L04) and the optical elements included in the common optical unit 282 (the lenses L05 and L06), are arranged along the single optical axis AX.

In this configuration, the light rays shown in FIG. 11 represent a situation in which parallel luminous flux emitted from the pupil position Pp of the subject eye 12 is formed by the second optical system 28A2 at the pupil conjugate position Pcj in the space at the opposite side of the second optical system 28A2 from the side at which the subject eye 12 is disposed. In this case, assuming that light from the fundus is emitted from the subject eye 12 as parallel luminous flux, the conjugate position of the fundus of the subject eye 12 is at the position marked as point Fcj in FIG. 11, which represents a primary spatial image of the fundus being formed between an annular concave reflection surface Mr01 and an annular convex reflection surface Mr02. Obviously, illumination beams (laser lights) from the respective units of the SLO unit 18 and OCT unit 20 described above are incident on the subject eye 12 in the form of parallel luminous flux centered on the pupil position Pp of the subject eye 12. The same applies in the practical examples described below.

The following Table 2 shows values of elements of the second optical system 28A2 according to the first practical example (practical example 1-2).

Table 2 represents a situation in which the effective field of view (the total illumination angle A from the pupil) is 100°-132° (a first surface incidence angle of 50°-66°) and the working distance WD is 18 mm. The overall length (a distance L2 from the pupil Pp position of the subject eye 12 to the pupil conjugate Pcj position) is 520.88 mm, and the pupil imaging magnification β1 from the pupil Pp position to the pupil conjugate Pcj position is 4.9×. A distortion factor M1 (a distortion factor of the maximum field of view at the fundus conjugate Fcj when an aplanatic ideal lens is included at the pupil conjugate Pcj position) is 0.574.

TABLE 2

| Surface Number | Lens Number | Radius of curvature (mm) | Surface separation (mm) | Refractive index Nd, dispersion Vd | Effective radius (mm) |
|---|---|---|---|---|---|
| | Subject eye | ∞ | ∞ | | |
| 1 (pupil surface) | D | ∞ | 18.00000 | | 1.00 |
| 2 | L01 | −242.47210 | 66.68069 | 1.48749, 70.3 | 35.55 |
| 3 | First reflection surface | −129.74184 | −66.68069 | 1.48749, 70.3 | 76.74 |
| 4 | Second reflection surface | −242.47210 | 66.68069 | 1.48749, 70.3 | 50.23 |
| 5 | | −129.74184 | 8.92625 | | 44.51 |
| 6 | L02 | −67.79268 | 7.20000 | 1.80809, 22.7 | 44.44 |
| 7 (aspherical surface) | | −86.34353 | 0.20000 | | 47.11 |
| 8 | L03 | 70.00000 | 12.00000 | 1.69680, 55.5 | 50.00 |
| 9 | L04 | 81.43144 | 7.00000 | 1.86074, 23.1 | 47.82 |
| 10 | | 68.11664 | 142.49494 | | 44.79 |
| 11 | L05 (common) | 158.55076 | 20.00000 | 1.49782, 82.6 | 46.63 |
| 12 | | −204.58045 | 24.91431 | | 45.92 |
| 13 | L06 (common) | −78.78320 | 20.00000 | 1.80809, 22.8 | 40.92 |
| 14 | | −92.55391 | 193.46853 | | 43.71 |
| Pupil conjugate | | | | | |

The aspherical surface coefficients representing the aspherical surface of surface 7 at lens L02 are as follows.

A=+0.398342E−06
B=−0.976217E−10
C=−0.544603E−13

Figure 12:
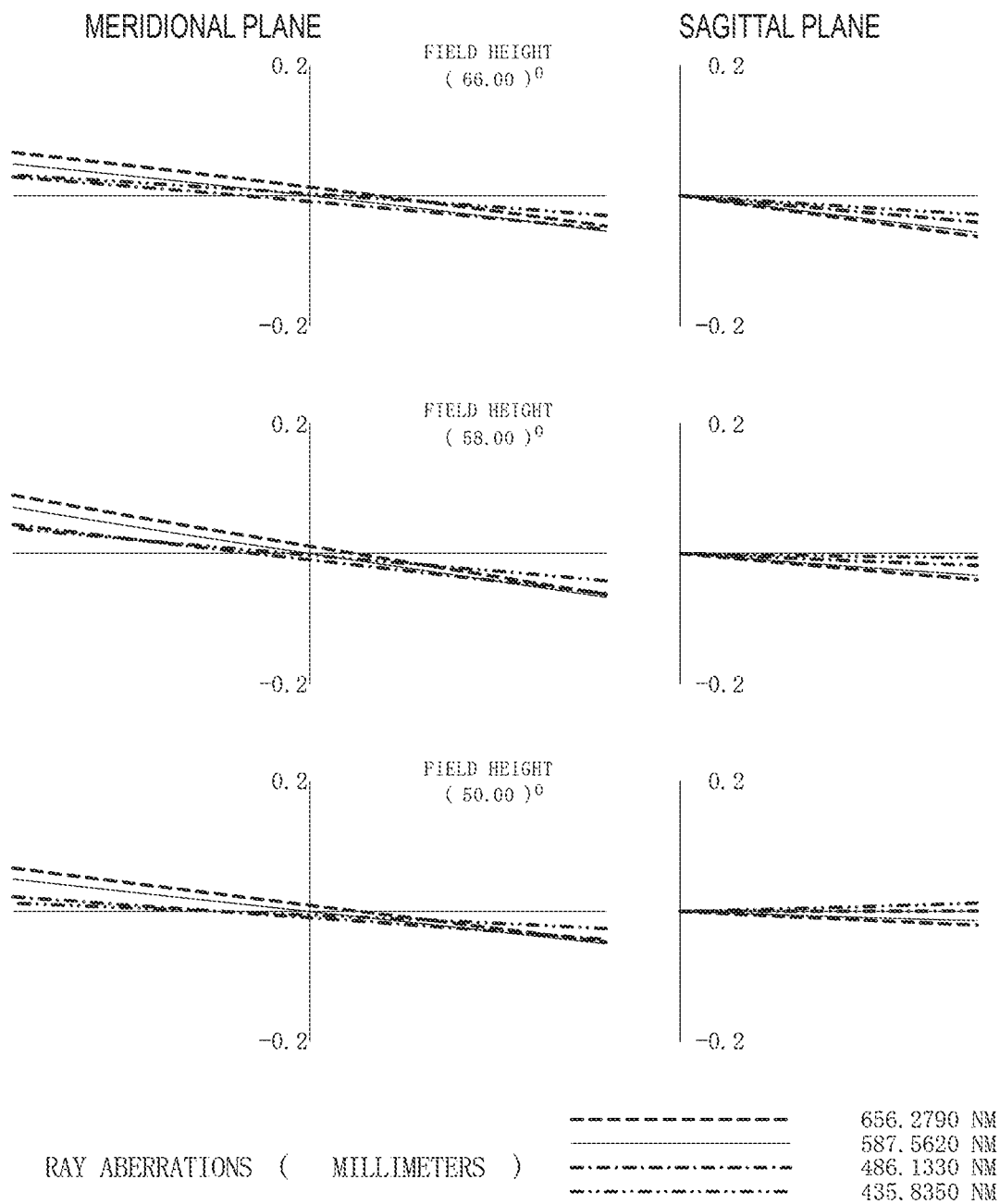
FIG. 12 is a lateral aberration diagram of the second optical system according to practical example 1-2.

FIG. 12 shows lateral aberration diagrams of the second optical system 28A2 configured in accordance with the elements in Table 2 (practical example 1-2). These lateral aberration diagrams are aberration diagrams of fundus images when an aplanatic ideal lens is suitably included at the pupil conjugate Pcj position, for evaluation of optical characteristics of the present practical example. Similarly in the practical examples described below, an aplanatic ideal lens is included and aberrations are calculated.

In the aberration diagrams shown in FIG. 12, the same as in FIG. 10, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 12, in the second optical system 28A2 according to the first practical example, variations in aberration for lights in the visible wavelength region are suppressed and are excellently corrected. It can also be seen that the second optical system 28A2 corrects excellently in the vicinity of the effective field of view (that is, the external illumination angle A) from 100°-110° (the first surface incidence angle of 50°-55°). Although not shown in the drawings, it can be verified that various other aberrations such as spherical aberration, astigmatism, distortion aberration and the like are also excellently corrected. Although not shown in the drawings, it can be verified that various other aberrations such as spherical aberration, astigmatism, distortion aberration and the like are also excellently corrected.

Figure 13:
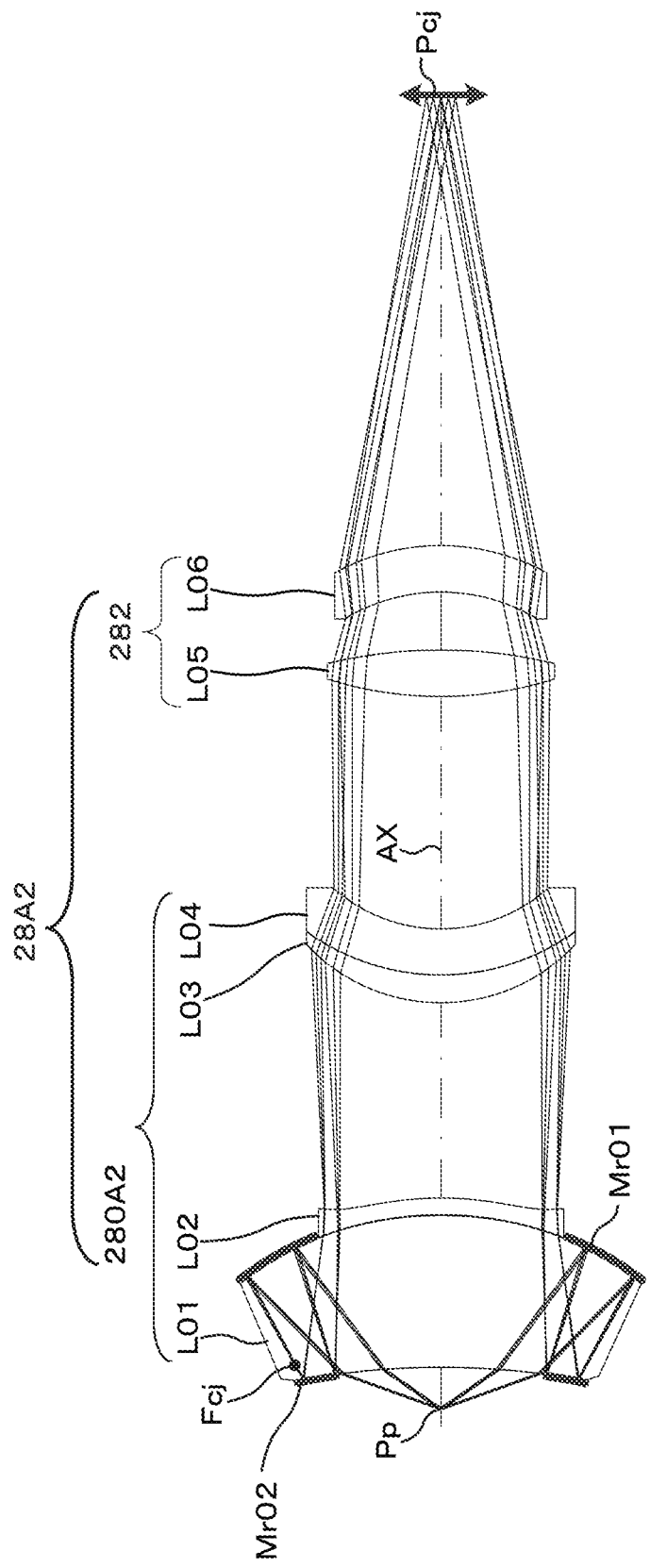
FIG. 13 is a structural diagram showing an example of a lens configuration of the second optical system according to practical example 1-3.

FIG. 13 shows a lens configuration of the second optical system 28A2 of the ophthalmic imaging apparatus 10 as practical example 1-3, which is a variant example of practical example 1-2.

In practical example 1-2, the respective effective fields of view (the total emission angles A from the pupil) of the first optical system 28A1 and the second optical system 28A2 are specified such that portions thereof (from 100° to 110°) overlap. In practical example 1-3, the effective fields of view are greater than in practical example 1-2 and the effective fields of view (the total emission angles A from the pupil) are specified so as to switch without overlapping.

The second optical system 28A2 includes the second optical unit 280A2. In the second optical unit 280A2, a positive meniscus lens L01, a negative meniscus lens L02 including an aspherical surface shape, a positive meniscus lens L03 and a negative meniscus lens L04 are arrayed in a lens group in this order from the side thereof at which the pupil Pp of the subject eye 12 is disposed. A concave surface of the positive meniscus lens L01 faces to the side at which the pupil surface D is disposed. A concave surface of the negative meniscus lens L02 at the side at which the pupil surface D is disposed is mated with a surface at the light emission side of the positive meniscus lens L01. A convex surface of the positive meniscus lens L03 faces to the side at which the pupil surface D is disposed. The negative meniscus lens L04 is mated with the positive meniscus lens L03. An optical system employed at the light emission side of the second optical unit 280A2 is used in common with the common optical unit 282 shown in FIG. 9.

The following Table 3 shows values of elements of the second optical system 28A2 according to the first practical example (practical example 1-3).

Table 3 represents a situation in which the effective field of view (the total illumination angle A from the pupil) is 110°-140° (a first surface incidence angle of 55°-70°) and the working distance WD is 18 mm. The overall length (the distance L2 from the pupil Pp position of the subject eye 12 to the pupil conjugate Pcj position) is 565 mm, and the pupil imaging magnification β2 from the pupil Pp position to the pupil conjugate Pcj position is 3.92×. The distortion factor M2 (the distortion factor of the maximum field of view at the fundus conjugate Fcj when the aplanatic ideal lens is included at the pupil conjugate Pcj position) is 0.720.

TABLE 3

| Surface Number | Lens Number | Radius of curvature (mm) | Surface separation (mm) | Refractive index Nd, dispersion Vd | Effective radius (mm) |
|---|---|---|---|---|---|
| | Subject eye | ∞ | ∞ | | |
| 1 (pupil surface) | D | ∞ | 18.00000 | | 1.00 |
| 2 | L01 | −329.21730 | 65.36435 | 1.48749, 70.3 | 42.78 |
| 3 (aspherical surface) | First reflection surface | −151.86751 | −65.36435 | 1.48749, 70.3 | 82.74 |
| 4 | Second reflection surface | −329.21730 | 65.36435 | 1.48749, 70.3 | 58.79 |
| 5 (aspherical surface) | | −151.86751 | 0.28342 | | 50.20 |
| 6 | L02 | −144.28176 | 7.20000 | 1.80809, 22.7 | 50.06 |
| 7 (aspherical surface) | | −128.90042 | 83.99201 | | 49.57 |
| 8 | L03 | 77.49241 | 12.00000 | 1.69680, 55.5 | 55.00 |
| 9 | L04 | 97.02421 | 19.77738 | 1.86074, 23.1 | 53.25 |
| 10 | | 68.16000 | 100.00000 | | 45.35 |
| 11 | L05 (common) | 158.55076 | 20.00000 | 1.49782, 82.6 | 46.28 |
| 12 | | −204.58045 | 24.91431 | | 45.54 |
| 13 | L06 (common | −78.78320 | 20.00000 | 1.80809, 22.8 | 40.47 |

The aspherical surface coefficients representing the aspherical surface of surface 3 and surface 5 at lens L01 are as follows.
A=−0.902137E−07
B=+0.794263E−11
C=−0.318956E−15 The aspherical surface coefficients representing the aspherical surface of surface 7 at lens L02 are as follows.
A=+0.585897E−06
B=−0.983043E−10
C=+0.117076E−12
D=−0.125282E−16

Figure 14:
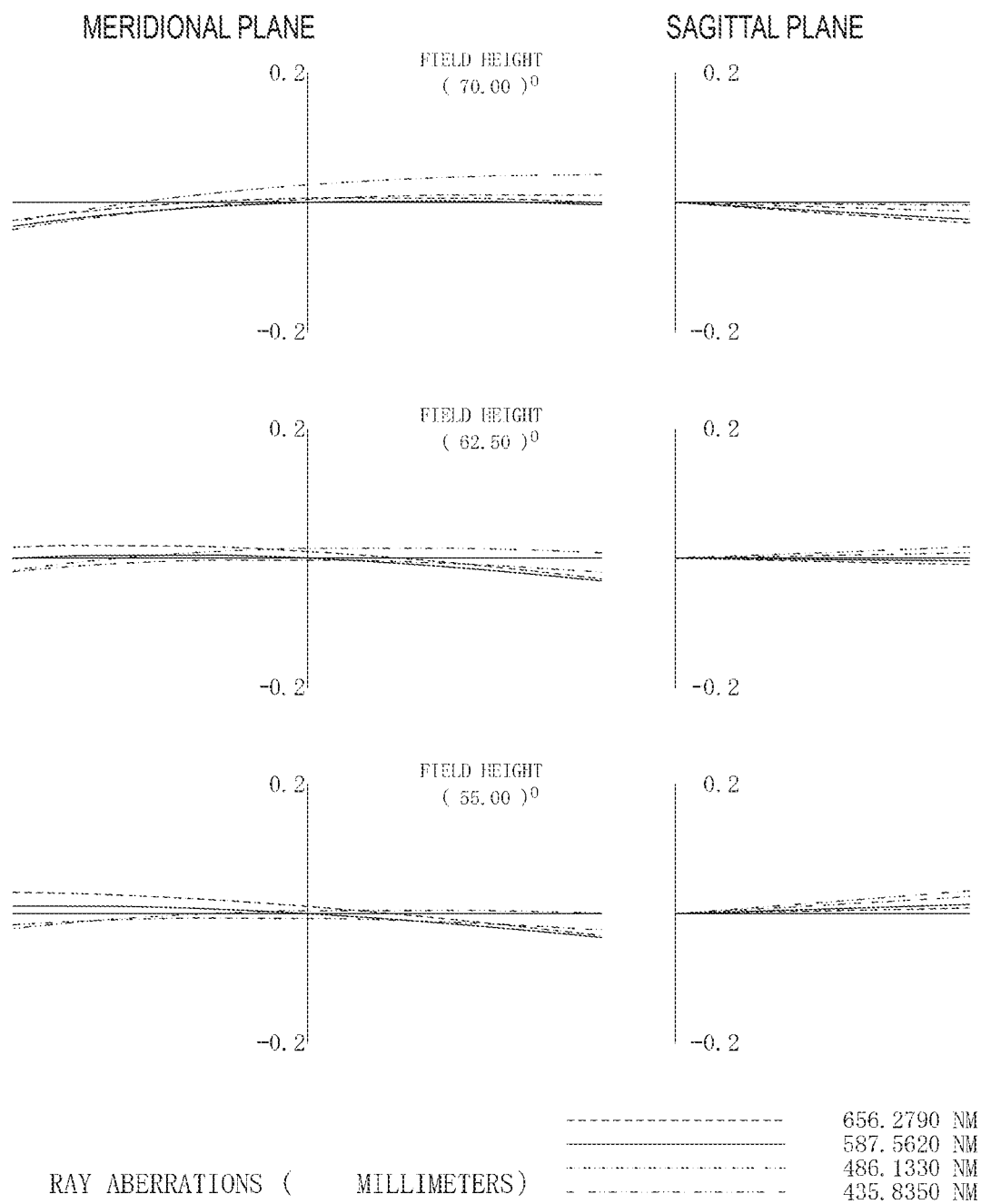
FIG. 14 is a lateral aberration diagram of the second optical system according to practical example 1-3.

FIG. 14 shows lateral aberration diagrams of the second optical system 28A2 configured in accordance with the elements in Table 3 (practical example 1-3).

In the aberration diagrams shown in FIG. 14, the same as in practical example 1, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 14, in the second optical system 28A2 according to the second practical example, variations in aberration for lights in the visible wavelength region are suppressed and are excellently corrected. It can also be seen that the second optical system 28A2 corrects more excellently than the first optical system 28A1 in the vicinity of the effective field of view at 110° (the first surface incidence angle of 55°). Although not shown in the drawings, it can be verified that various other aberrations such as spherical aberration, astigmatism, distortion aberration and the like are also excellently corrected.

Second Practical Example

Now, a second practical example is described. In the first practical example, lens elements with aspherical surface shapes are included in both the first optical system 28A1 and the second optical system 28A2. In the second practical example, all of the lens elements constituting the first optical system 28A1 that is pertinent to the field of view of the fundus central portion centered on the optical axis are specified with spherical surface shapes. Further, in the second practical example, the effective field of views (the total emission angles A from the pupil) of the first optical system 28A1 and the second optical system 28A2 are specified so as to switch without overlapping.

The second practical example has a similar structure to the first practical example. Accordingly, structures that are the same are assigned the same reference symbols and are not described in detail here.

Figure 15:
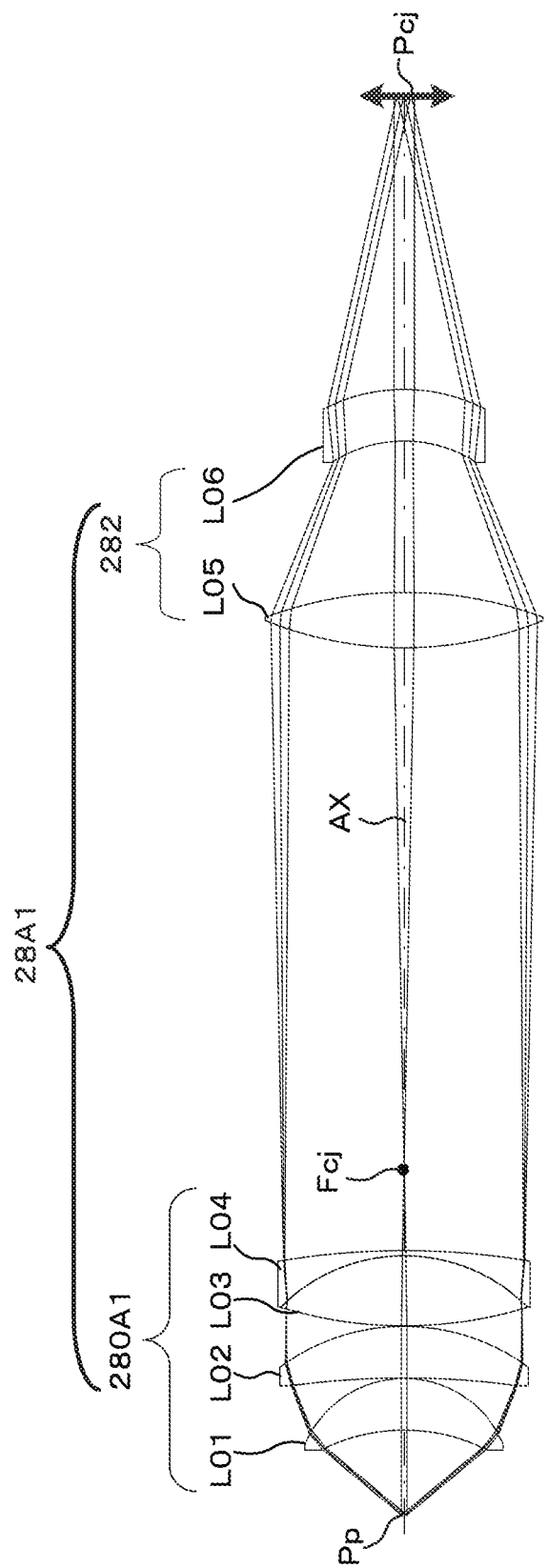
FIG. 15 is a structural diagram showing an example of a lens configuration of the first optical system according to practical example 2-1.

FIG. 15 shows a lens configuration of the first optical system 28A1 of the ophthalmic imaging apparatus 10 according to the second practical example, which is illustrated as practical example 2-1.

The first optical system 28A1 includes the first optical unit 280A1. In the first optical unit 280A1, a positive meniscus lens L01, a positive meniscus lens L02, a convex lens L03 and a negative meniscus lens L04 are arrayed in a lens group in this order from the side thereof at which the pupil Pp of the subject eye 12 is disposed. A concave surface of the positive meniscus lens L01 faces to the side at which the pupil surface D is disposed. A concave surface of the negative meniscus lens L02 faces to the side at which the pupil surface D is disposed. The negative meniscus lens L04 is mated with the convex lens L03 at the side of the negative meniscus lens L04 at which the pupil surface D is disposed. The first optical system 28A1 also includes the common optical unit 282 at the light emission side of the first optical unit 280A1. In the common optical unit 282, a convex lens L05 and a negative meniscus lens L06 are arrayed in this order from the side thereof at which the pupil Pp of the subject eye 12 is disposed. A concave surface of the negative meniscus lens L06 faces to the side at which the pupil surface D is disposed.

All of the optical elements constituting the first optical system 28A1, which is to say the optical elements included in the first optical unit 280A1 (the lenses L01, L02, L03 and L04) and the optical elements included in the common optical unit 282 (the lenses L05 and L06), are arranged along a single optical axis AX.

The following Table 4 shows values of elements of the first optical system 28A1 according to the second practical example (practical example 2-1).

Table 4 represents a situation in which the effective field of view (the total emission angle A from the pupil) is 0°-100° (a first surface incidence angle of 0°-50°) and the working distance WD is 32.99 mm. The overall length (the distance L1 from the pupil Pp position of the subject eye 12 to the pupil conjugate Pcj position) is 550 mm, and the pupil imaging magnification β1 from the pupil Pp position to the pupil conjugate Pcj position is 3.95×. The distortion factor M1 (the distortion factor of the maximum field of view at the fundus conjugate Fcj when an aplanatic ideal lens is included at the pupil conjugate Pcj position) is 0.268.

TABLE 4

| Surface Number | Lens Number | Radius of curvature (mm) | Surface separation (mm) | Refractive index Nd, dispersion Vd | Effective radius (mm) |
|---|---|---|---|---|---|
| Subject eye | | ∞ | ∞ | | |
| 1 (pupil surface) | D | ∞ | 32.98885 | | 1.00 |
| 2 | L01 | −70.00000 | 20.00000 | 1.75500, 52.3 | 31.43 |
| 3 | | −41.23614 | 0.20000 | | 36.27 |
| 4 | L02 | −313.73652 | 20.00000 | 1.75500, 52.3 | 43.40 |
| 5 | | −80.15938 | 0.20000 | | 45.75 |
| 6 | L03 | 159.75103 | 27.11797 | 1.49782, 82.6 | 45.36 |
| 7 | L04 | −66.70838 | 2.00000 | 1.80809, 22.8 | 45.09 |
| 8 | | −292.22565 | 233.58991 | | 46.39 |
| 9 | L05 (common) | 140.25105 | 21.45278 | 1.49782, 82.6 | 51.24 |
| 10 | | −152.27739 | 58.59737 | | 50.89 |
| 11 | L06 | −50.61851 | 20.00000 | 1.80809, 22.8 | 27.22 |
| 12 First pupil conjugate | (common) | −67.17169 | 113.85311 | | 29.39 |

Figure 16:
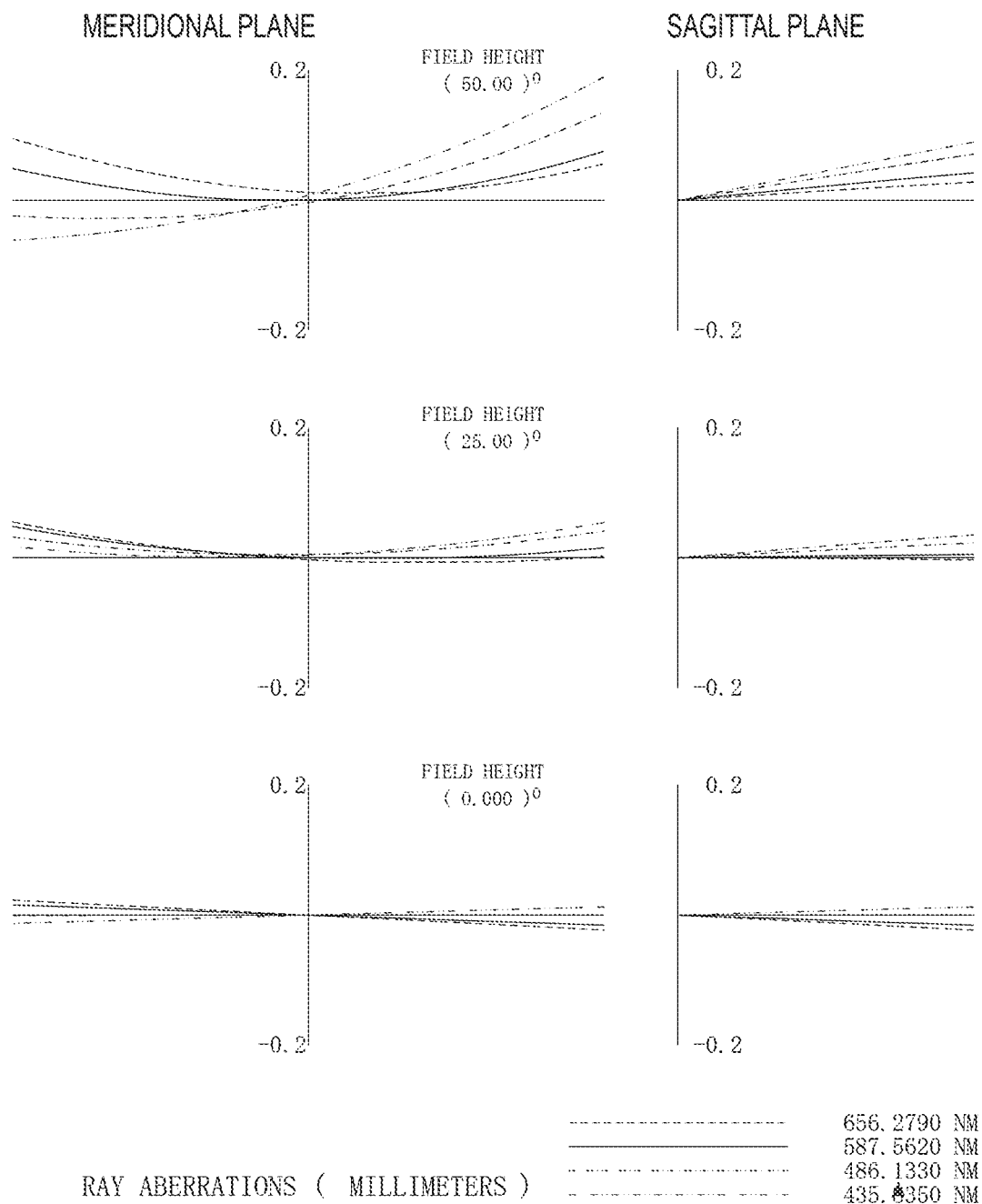
FIG. 16 is a lateral aberration diagram of the first optical system according to practical example 2-1.

FIG. 16 shows lateral aberration diagrams of the first optical system 28A1 configured in accordance with the elements in Table 4 (practical example 2-1).

In the aberration diagrams shown in FIG. 16, the same as in practical example 1, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 16, in the first optical system 28A1 according to the third practical example, aberrations increase with the size of the effective field of view.

Figure 17:
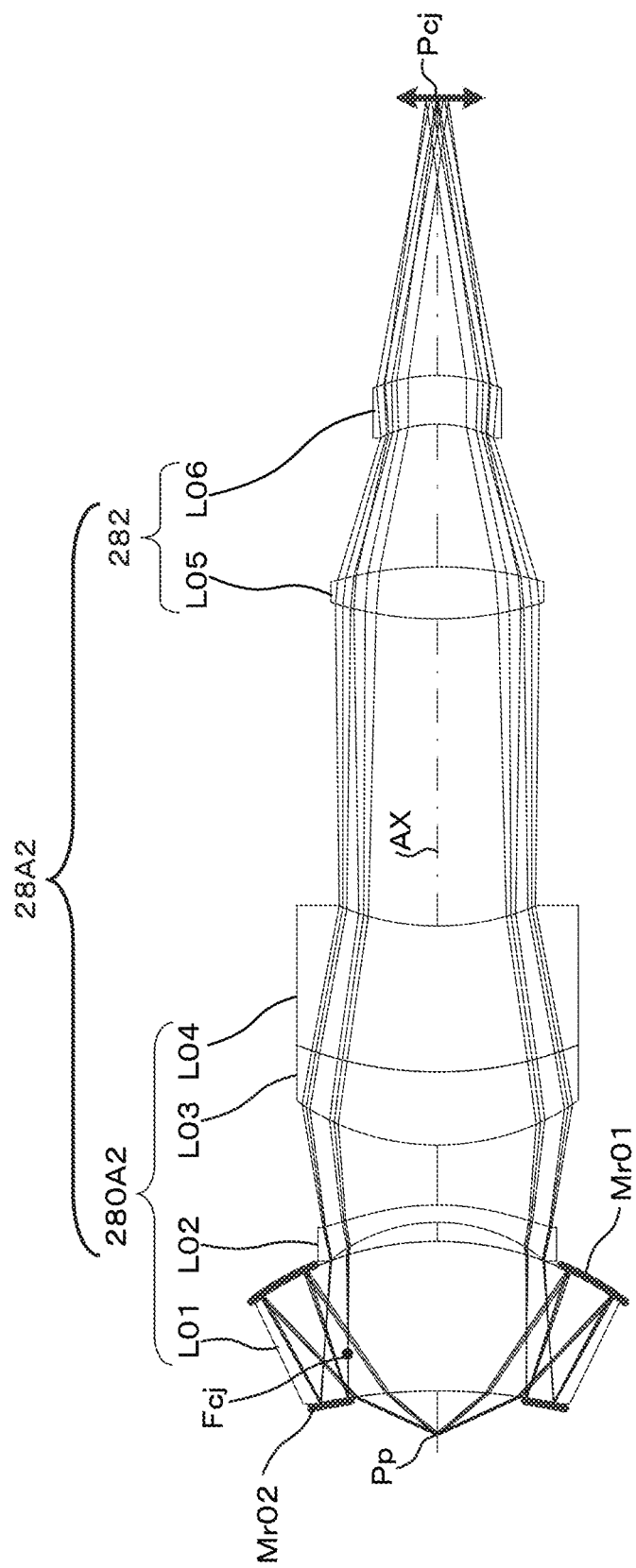
FIG. 17 is a structural diagram showing an example of a lens configuration of the second optical system according to practical example 2-2.

FIG. 17 shows a lens configuration of the second optical system 28A2 of the ophthalmic imaging apparatus 10 according to the second practical example, which is illustrated as practical example 2-2.

The second optical system 28A2 according to practical example 2-2 includes the second optical unit 280A2. In the second optical unit 280A2, a positive meniscus lens L01, a negative meniscus lens L02 including an aspherical surface shape, a positive meniscus lens L03 and a negative meniscus lens L04 are arrayed in a lens group in this order from the side thereof at which the pupil Pp of the subject eye 12 is disposed. A concave surface of the positive meniscus lens L01 faces to the side at which the pupil surface D is disposed. A concave surface of the negative meniscus lens L02 faces to the side at which the pupil surface D is disposed. A convex surface of the positive meniscus lens L03 faces to the side at which the pupil surface D is disposed. The negative meniscus lens L04 is mated with the positive meniscus lens L03. An optical system employed at the light emission side of the second optical unit 280A2 is used in common with the common optical unit 282 shown in FIG. 15.

The same as in the first optical system 28A1, all of the optical elements constituting the second optical system 28A2, which is to say the optical elements included in the second optical unit 280A2 (the lenses L01, L02, L03 and L04) and the optical elements included in the common optical unit 282 (the lenses L05 and L06), are arranged along the single optical axis AX.

The following Table 5 shows values of elements of the second optical system 28A2 according to the second practical example (practical example 2-2).

Table 5 represents a situation in which the effective field of view (the total emission angle A from the pupil) is 100°-130° (a first surface incidence angle of 50°-65°) and the working distance WD is 18 mm. The overall length (the distance L2 from the pupil Pp position of the subject eye 12 to the pupil conjugate Pcj position) is 549.19 mm, and the pupil imaging magnification β2 from the pupil Pp position to the pupil conjugate Pcj position is 5.64×. The distortion factor M2 (the distortion factor of the maximum field of view at the fundus conjugate Fcj when an aplanatic ideal lens is included at the pupil conjugate Pcj position) is 0.517.

TABLE 5

| Surface Number | Lens Number | Radius of curvature (mm) | Surface separation (mm) | Refractive index Nd, dispersion Vd | Effective radius (mm) |
|---|---|---|---|---|---|
| Subject eye pupil | | ∞ | ∞ | | |
| 1 | D | ∞ | 18.00000 | | 1.00 |
| 2 | L01 | −225.23197 | 61.38739 | 1.48749, 70.3 | 34.05 |
| 3 | First reflection surface | −122.43666 | −61.38739 | 1.48749, 70.3 | 71.70 |
| 4 | Second reflection surface | −225.23197 | 61.38739 | 1.48749, 70.3 | 47.71 |
| 5 | | −122.43666 | 7.81275 | | 43.58 |
| 6 | L02 | −68.39584 | 7.20000 | 1.80809, 22.7 | 43.52 |
| 7 (aspherical surface) | | −98.42014 | 24.67075 | | 46.41 |
| 8 | L03 | 99.15145 | 30.00000 | 1.69680, 55.5 | 55.00 |
| 9 | L04 | 154.32713 | 60.00000 | 1.86074, 23.1 | 51.17 |
| 10 | | 101.00880 | 126.21633 | | 39.95 |
| 11 | L05 (common) | 140.25105 | 21.45278 | 1.49782, 82.6 | 41.43 |
| 12 | | −152.27739 | 58.59737 | | 40.51 |
| 13 | L06 (common) | −50.61851 | 20.00000 | 1.80809, 22.8 | 22.95 |
| 14 | | −67.17169 | 113.85311 | | 24.59 |
| First pupil conjugate | | | | | |

The aspherical surface coefficients representing the aspherical surface of surface 7 at lens L02 are as follows.

A=+0.505045E−06
B=−0.185139E−09
C=+0.118203E−12
D=−0.133097E−16

Figure 18:
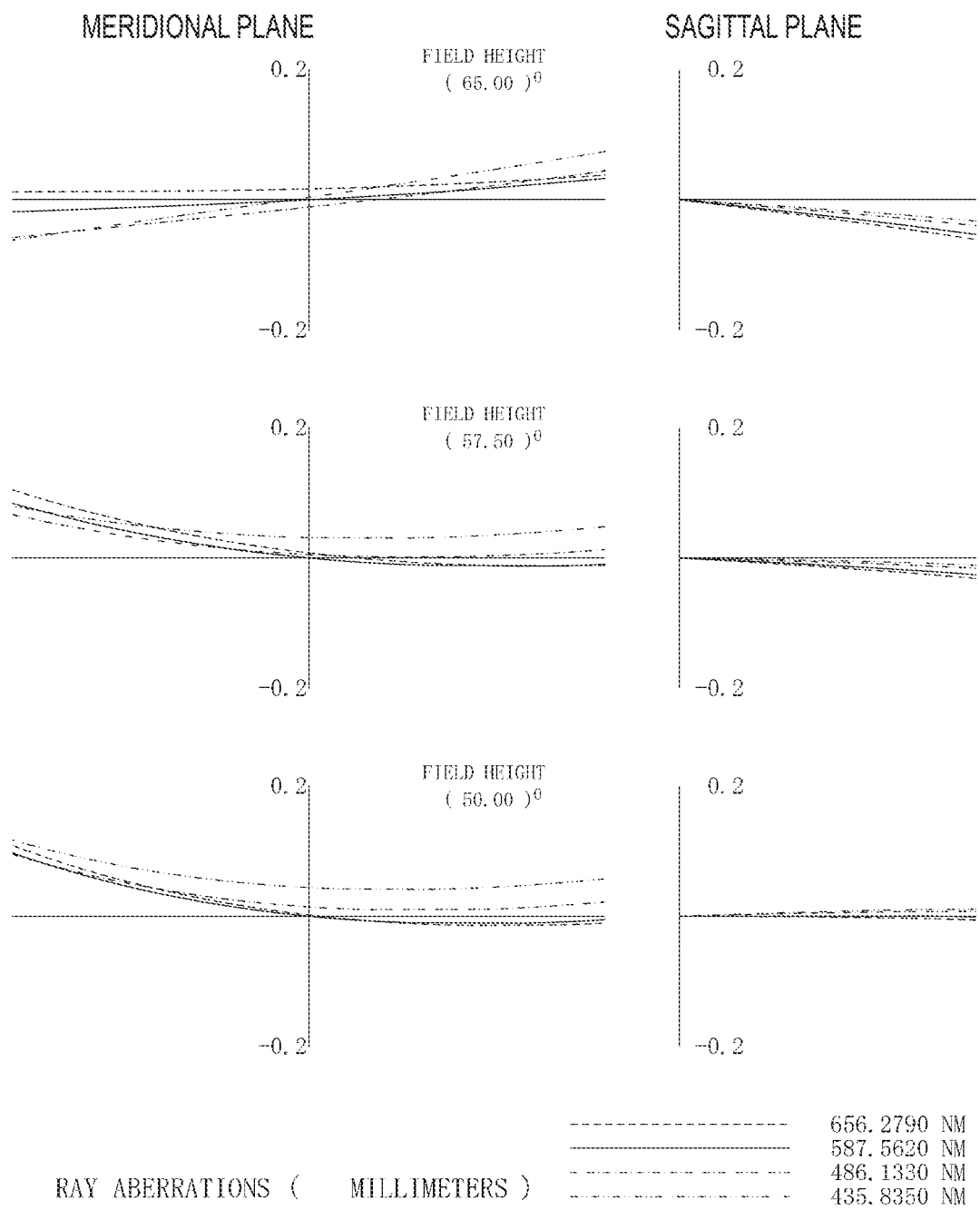
FIG. 18 is a lateral aberration diagram of the second optical system according to practical example 2-2.

FIG. 18 shows lateral aberration diagrams of the second optical system 28A2 configured in accordance with the elements in Table 2 (practical example 2-2).

In the aberration diagrams shown in FIG. 18, the same as in the first practical example, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 18, in the second optical system 28A2 according to practical example 2-2, variations in aberration for lights in the visible wavelength region are suppressed and are excellently corrected by the first optical system 28A1 in the vicinity of the effective field of view at 100° (the first surface incidence angle of 50°). Although not shown in the drawings, it can be verified that various other aberrations such as spherical aberration, astigmatism, distortion aberration and the like are also excellently corrected.

Now, a variant example is described.

In the variant example, when it is assumed both that the aperture diameter of the lens elements is to be small and that the aperture diameter of the reflection surfaces is to be small, the configuration is formed with the emphasis on reducing the aperture diameter of the lens elements. More specifically, emphasis is put on making the aperture diameter of the lens elements smaller, while an increase in size of the reflection surfaces may be tolerated to some extent. To provide a wide-angle field of view, a catadioptric optical system that serves as the second optical unit structuring the second optical unit 280A2 is realized by including a positive meniscus lens at the side of the second optical unit that is closest to the subject eye. A concave surface of the positive meniscus lens faces to the side thereof at which the subject eye is disposed. In order of incidence of light from the side of the second optical unit at which the pupil Pp of the subject eye 12 is disposed, the second optical unit is also configured with a refracting lens with a positive refractivity, a first reflection surface, a second reflection surface, and a refracting lens with a negative refractivity. The first reflection surface is a surface-reflecting surface with gas at the incidence side thereof and includes a central aperture. The second reflection surface is a surface-reflecting surface with gas at the incidence side thereof. Via the central aperture of the first reflection surface, an image is formed at the position of the pupil conjugate Pcj that is conjugate with the pupil Pp position of the subject eye 12. In this configuration, it is preferable to dispose the lens with the negative refractivity between the first reflection surface and the second reflection surface.

Practical examples described below have similar structures to the first practical example and the second practical example. Accordingly, structures that are the same are assigned the same reference symbols and are not described in detail here.

Third Practical Example

Figure 19:
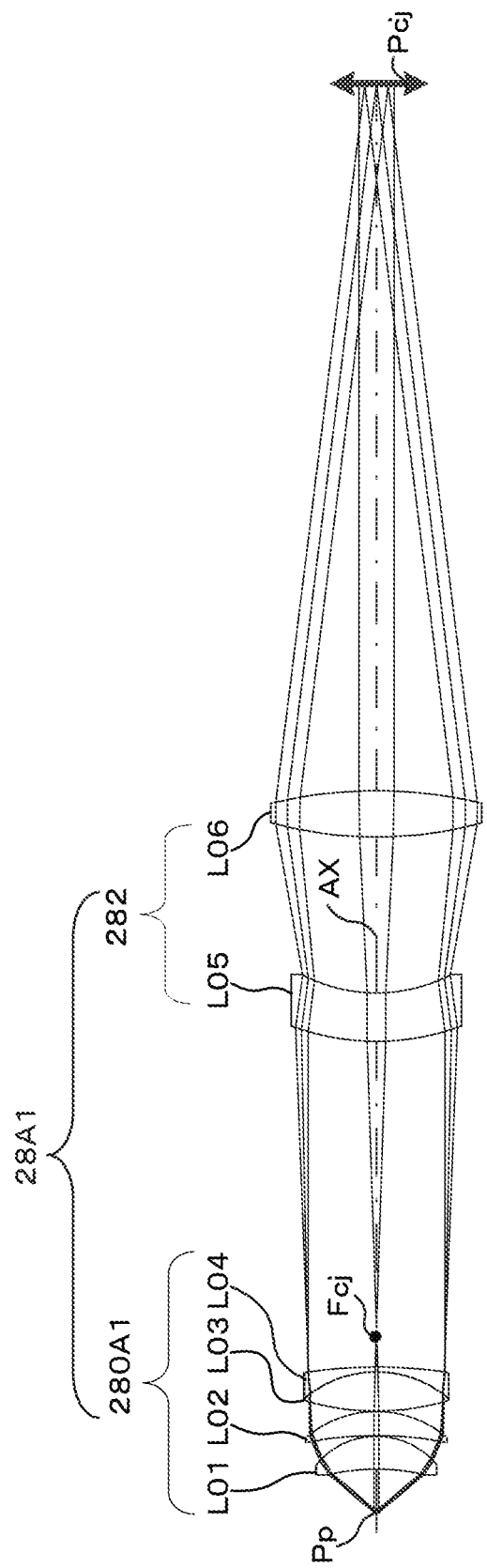
FIG. 19 is a structural diagram showing an example of a lens configuration of the first optical system according to practical example 3-1.

FIG. 19 shows a lens configuration of the first optical system 28A1 according to the third practical example, which is illustrated as practical example 3-1. In practical example 3-1, the aperture diameter of lens elements in the first optical system 28A1 is made smaller.

The first optical system 28A1 includes the first optical unit 280A1. In the first optical unit 280A1, a positive meniscus lens L01, a positive meniscus lens L02 with an aspherical surface shape, a convex lens L03 and a negative meniscus lens L04 are arrayed in a lens group in this order from the side thereof at which the pupil Pp of the subject eye 12 is disposed. A concave surface of the positive meniscus lens L01 faces to the side at which the pupil surface D is disposed. A concave surface of the negative meniscus lens L02 faces to the side at which the pupil surface D is disposed. The negative meniscus lens L04 is mated with the convex lens L03 at the side of the negative meniscus lens L04 at which the pupil surface D is disposed. The first optical system 28A1 also includes the common optical unit 282 at the light emission side of the first optical unit 280A1. In the common optical unit 282, a negative meniscus lens L05 and a convex lens L06 are arrayed in this order from the side thereof at which the pupil Pp of the subject eye 12 is disposed. A concave surface of the negative meniscus lens L05 faces to the side at which the pupil surface D is disposed.

All of the optical elements constituting the first optical system 28A1, which is to say the optical elements included in the first optical unit 280A1 (the lenses L01, L02, L03 and L04) and the optical elements included in the common optical unit 282 (the lenses L05 and L06), are arranged along the single optical axis AX.

The following Table 6 shows values of elements of the first optical system 28A1 according to the second practical example (practical example 3-1).

Table 6 represents a situation in which the effective field of view (the total emission angle A from the pupil) is 0°-100° (a first surface incidence angle of 0°-50°) and the working distance WD is 18.0 mm. The overall length (the distance L1 from the pupil Pp position of the subject eye 12 to the pupil conjugate Pcj position) is 590 mm, and the pupil imaging magnification β1 from the pupil Pp position to the pupil conjugate Pcj position is 7.24×. The distortion factor M1 (the distortion factor of the maximum field of view at the fundus conjugate Fcj when an aplanatic ideal lens is included at the pupil conjugate Pcj position) is 0.249.

TABLE 6

| Surface Number | Lens Number | Radius of curvature (mm) | Surface separation (mm) | Refractive index Nd, dispersion Vd | Effective radius (mm) |
|---|---|---|---|---|---|
| Subject eye | | ∞ | ∞ | | |
| 1 (pupil surface) | D | ∞ | 18.00000 | | 1.50 |
| 2 | L01 | −85.45305 | 13.56908 | 1.75500, 52.3 | 20.10 |
| 3 | | −31.65578 | 0.20000 | | 23.63 |
| 4 (aspherical surface) | L02 | −194.86535 | 9.97954 | 1.75500, 52.3 | 26.84 |
| 5 | | −44.53840 | 0.20000 | | 27.77 |
| 6 | L03 | 102.08359 | 16.17555 | 1.49782, 82.6 | 27.89 |
| 7 | L04 | −45.46215 | 2.00000 | 1.80809, 22.8 | 27.64 |
| 8 | | −193.33552 | 134.43305 | | 28.20 |
| 9 | L05 (common) | 100.00000 | 20.00000 | 1.80809, 22.8 | 34.52 |
| 10 | | 66.31289 | 64.36818 | | 31.54 |
| 11 | L06 (common) | 163.38309 | 19.05397 | 1.59319, 67.9 | 43.88 |
| 12 First pupil conjugate | | −185.81582 | 292.02062 | | 43.99 |

Figure 20:
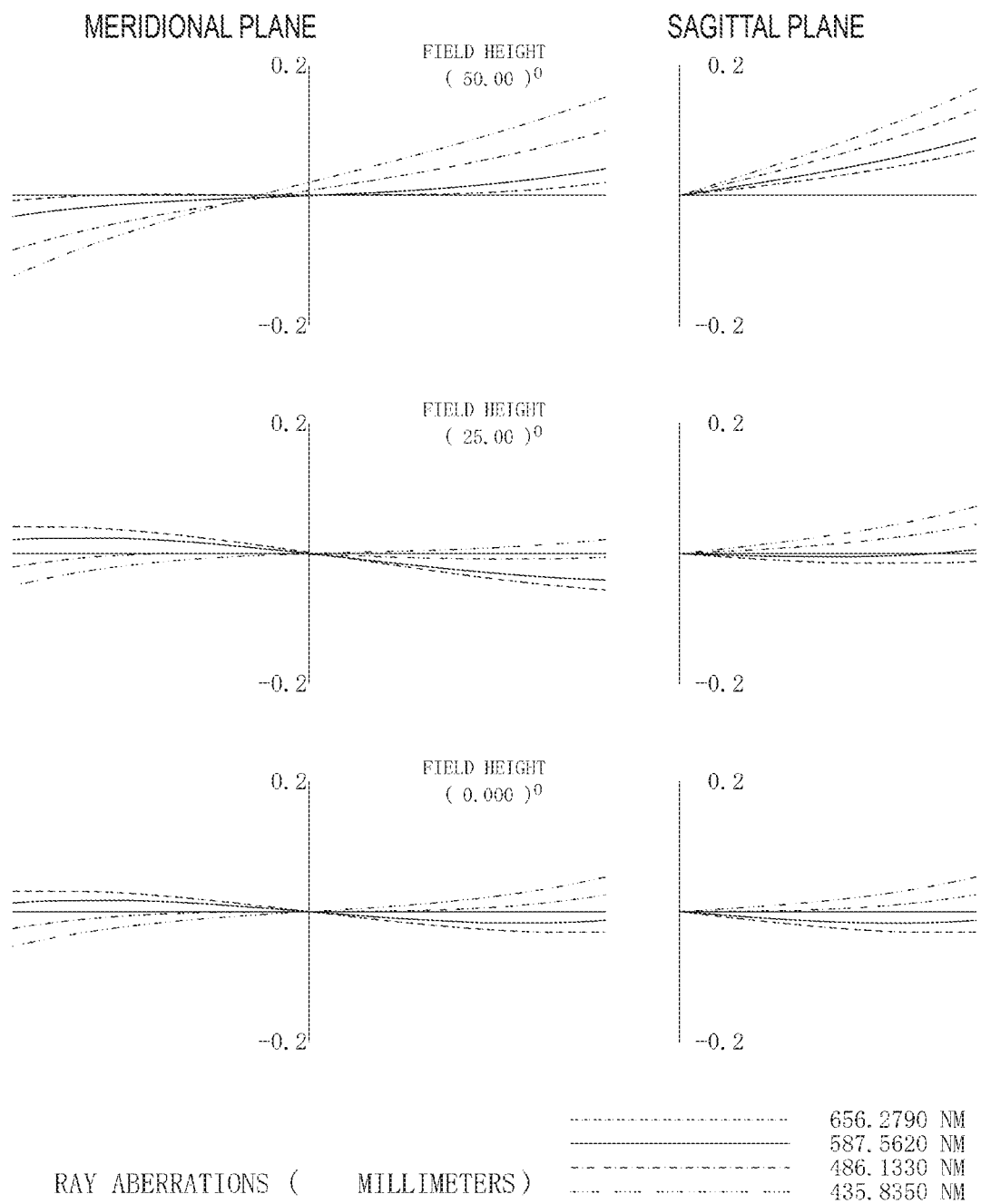
FIG. 20 is a lateral aberration diagram of the first optical system according to practical example 3-1.

FIG. 20 shows lateral aberration diagrams of the first optical system 28A1 configured in accordance with the elements in Table 6 (practical example 3-1).

In the aberration diagrams shown in FIG. 20, the same as above, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 20, in the first optical system 28A1 according to the practical example 3-1, aberrations increase with the size of the effective field of view.

Figure 21:
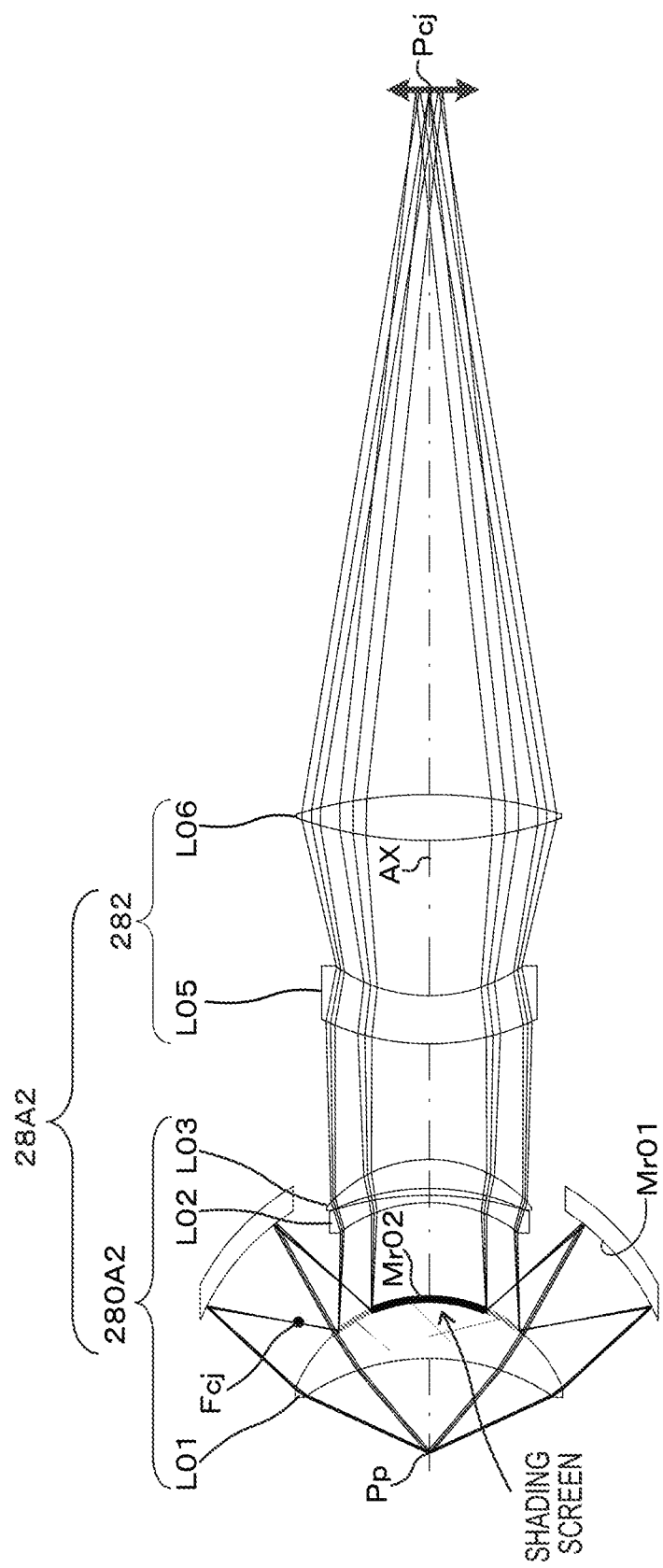
FIG. 21 is a structural diagram showing an example of a lens configuration of the second optical system according to practical example 3-2.

FIG. 21 shows a lens configuration of the second optical system 28A2 of the ophthalmic imaging apparatus 10 according to the third practical example, which is illustrated as practical example 3-2.

The second optical system 28A2 according to practical example 3-2 includes the second optical unit 280A2. In the second optical unit 280A2, a positive meniscus lens L01, an annular first reflection surface Mr01, a second reflection surface Mr02, a negative meniscus lens L02 and a positive meniscus lens L03 are arrayed in this order from the side thereof at which the pupil Pp of the subject eye 12 is disposed. A concave surface of the positive meniscus lens L01 faces to the side at which the pupil surface D is disposed. A concave surface of the first reflection surface Mr01 faces to the side at which the pupil surface D is disposed. The second reflection surface Mr02 is provided at a central portion of a convex surface of the positive meniscus lens L01. A concave surface of the negative meniscus lens L02 faces to the side at which the pupil surface D is disposed. A concave surface of the positive meniscus lens L03 faces to the side at which the pupil surface D is disposed. An optical system employed at the light emission side of the second optical unit 280A2 is used in common with the common optical unit 282 shown in FIG. 19.

The same as in the first optical system 28A1, all of the optical elements constituting the second optical system 28A2, which is to say the optical elements included in the second optical unit 280A2 (the lenses L01, L02 and L03) and the optical elements included in the common optical unit 282 (the lenses L05 and L06), are arranged along the single optical axis AX.

The following Table 7 shows values of elements of the second optical system 28A2 according to practical example 3-2 (practical example 3-2).

Table 7 represents a situation in which the effective field of view (the total emission angle A from the pupil) is 80°-130° (a first surface incidence angle of 40°-65°) and the working distance WD is 39.1089 mm. The overall length (the distance L2 from the pupil Pp position of the subject eye 12 to the pupil conjugate Pcj position) is 565 mm, and the pupil imaging magnification β2 from the pupil Pp position to the pupil conjugate Pcj position is 6.4×. The distortion factor M2 (the distortion factor of the maximum field of view at the fundus conjugate Fcj when an aplanatic ideal lens is included at the pupil conjugate Pcj position) is 0.518.

TABLE 7

| Surface Number | Lens Number | Radius of curvature (mm) | Surface separation (mm) | Refractive index Nd, dispersion Vd | Effective radius (mm) |
|---|---|---|---|---|---|
| Subject eye pupil | | ∞ | ∞ | | |
| 1 | D | ∞ | 39.10890 | | 1.00 |
| 2 | L01 | −89.22313 | 24.61018 | 1.49782, 82.6 | 50.81 |
| 3 | | −59.08816 | 53.10935 | | 55.00 |
| 4 | First reflection surface | −101.99977 | −53.10935 | | 91.40 |
| 5 | Second reflection surface | −59.08816 | 40.00000 | | 37.19 |
| 6 | L02 | −60.00000 | 3.00000 | 1.76182, 26.6 | 36.36 |
| 7 | | −127.94213 | 2.86962 | | 39.09 |
| 8 | L03 | −91.58806 | 11.96633 | 1.49782, 82.6 | 39.15 |
| 9 | | −54.33130 | 48.00224 | | 40.17 |
| 10 | L05 (common) | 100.00000 | 20.00000 | 1.80809, 22.8 | 42.26 |
| 11 | | 66.31289 | 64.36818 | | 38.00 |
| 12 | L06 (common) | 163.38309 | 19.05397 | | 52.20 |
| 13 First pupil conjugate | | −185.81582 | 292.02062 | | 52.23 |

Figure 22:
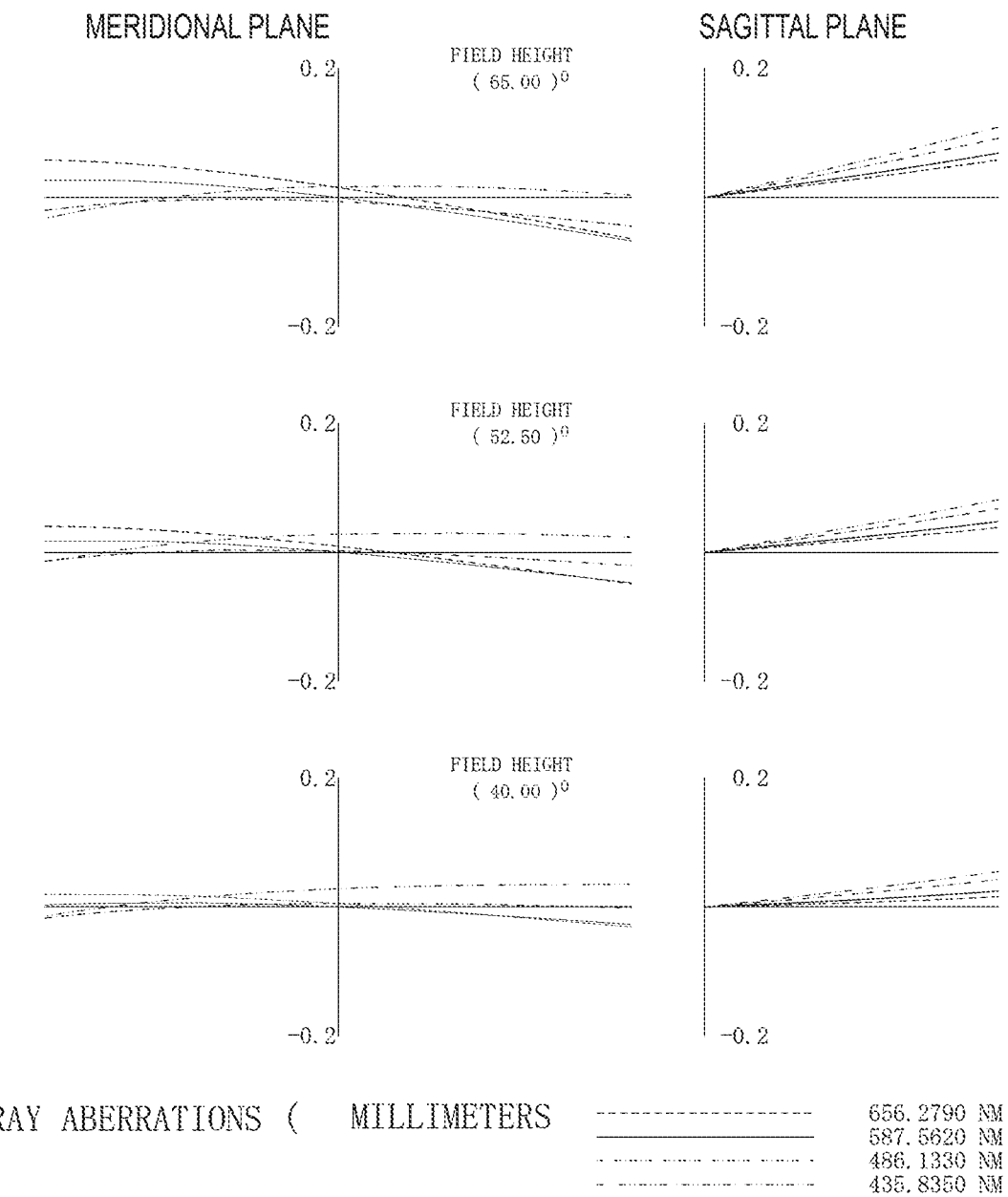
FIG. 22 is a lateral aberration diagram of the second optical system according to practical example 3-2.

FIG. 22 shows lateral aberration diagrams of the second optical system 28A2 configured in accordance with the elements in Table 7 (practical example 3-2).

In the aberration diagrams shown in FIG. 22, the same as in the first practical example, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 22, in the second optical system 28A2 according to the third practical example, variations in aberration for lights in the visible wavelength region are suppressed and are excellently corrected by the first optical system 28A1 in the vicinity of the effective field of view at 100° (the first surface incidence angle of 50°). Although not shown in the drawings, it can be verified that various other aberrations such as spherical aberration, astigmatism, distortion aberration and the like are also excellently corrected.

Figure 23:
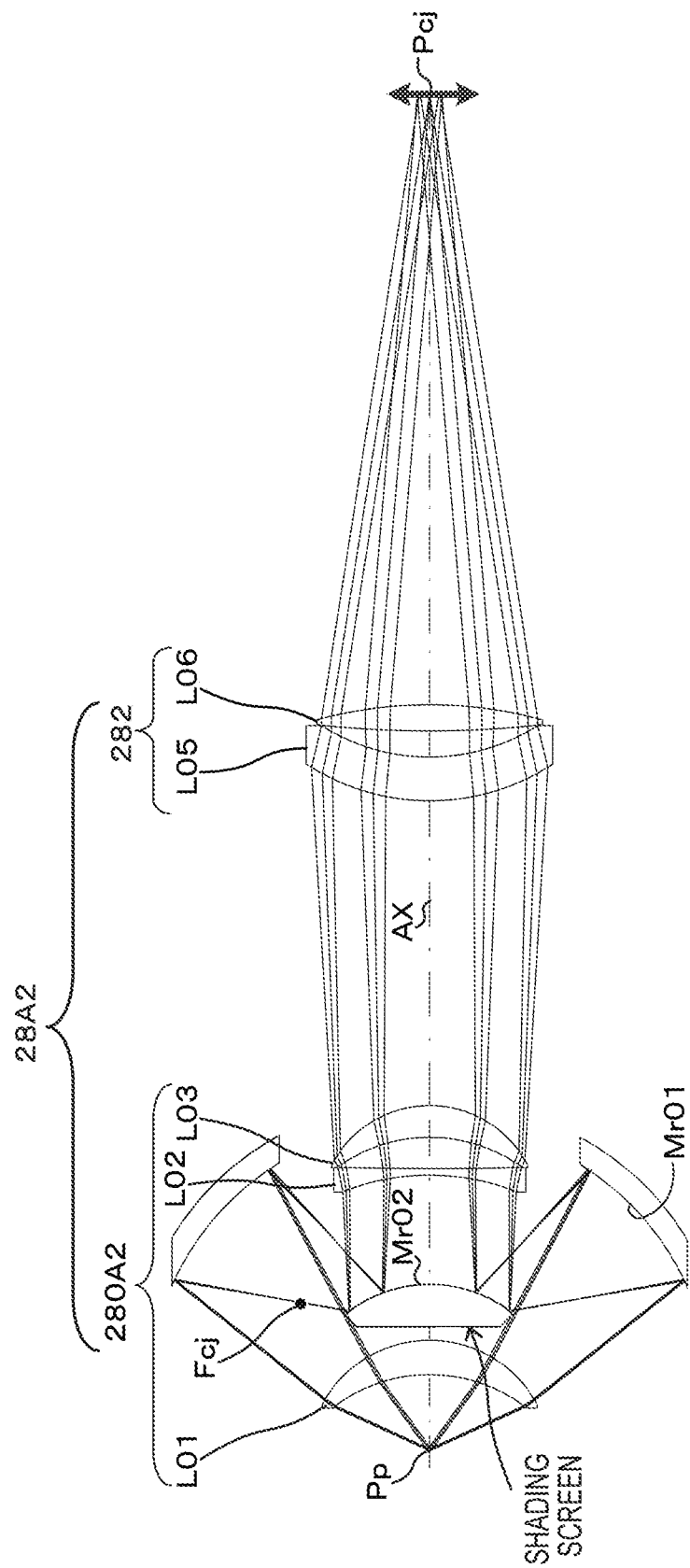
FIG. 23 is a structural diagram showing an example of a lens configuration of the second optical system according to practical example 3-3.

FIG. 23 shows a lens configuration of the second optical system 28A2 of the ophthalmic imaging apparatus 10 as practical example 3-3, which is a variant example of practical example 3-2. In practical example 3-2 the second reflection surface Mr02 is provided at the central portion of the convex surface of the positive meniscus lens L01, but in practical example 3-3 the second reflection surface Mr02 is provided at an element separate from a positive meniscus lens L01.

The second optical system 28A2 according to practical example 3-3 includes the second optical unit 280A2. In the second optical unit 280A2, the positive meniscus lens L01, an annular first reflection surface Mr01 including an aspherical surface shape, a second reflection surface Mr02 including an aspherical surface shape, a negative meniscus lens L02 and a positive meniscus lens L03 are arrayed in this order from the side thereof at which the pupil Pp of the subject eye 12 is disposed. A concave surface of the positive meniscus lens L01 faces to the side at which the pupil surface D is disposed. A concave surface of the first reflection surface Mr01 faces to the side at which the pupil surface D is disposed. The second reflection surface Mr02 is provided at a central portion of a convex surface at the opposite side from the side thereof at which the pupil surface D is disposed. A concave surface of the negative meniscus lens L02 faces to the side at which the pupil surface D is disposed. A concave surface of the positive meniscus lens L03 faces to the side at which the pupil surface D is disposed. The first optical system 28A1 also includes the common optical unit 282 at the light emission side of the second optical unit 280A2. In the common optical unit 282, a negative meniscus lens L05 and a convex lens L06 are arrayed in this order from the side thereof at which the pupil Pp of the subject eye 12 is disposed. A convex surface of the negative meniscus lens L05 faces to the side at which the pupil surface D is disposed. The lens configuration of the common optical unit 282 at the rear of practical example 3-3 differs from practical example 3-1 (FIG. 19) and practical example 3-2 (FIG. 21) described above and is not compatible therewith. Therefore, it is necessary to implement switching between the circular field of view and the annular field of view surrounding the circular field of view by respectively integrally switching the entire lens system between the second optical system 28A2 according to practical example 3-3 (FIG. 23) and the first optical system 28A1 according to practical example 3-1.

The following Table 8 shows values of elements of the second optical system 28A2 according to the third practical example (practical example 3-3).

Table 8 represents a situation in which the effective field of view (the total emission angle A from the pupil) is 70°-130° (a first surface incidence angle of 35°-65°) and the working distance WD is 34.448 mm. The overall length (the distance L2 from the pupil Pp position of the subject eye 12 to the pupil conjugate Pcj position) is 620 mm, and the pupil imaging magnification β2 from the pupil Pp position to the pupil conjugate Pcj position is 7.6×. The distortion factor M2 (the distortion factor of the maximum field of view at the fundus conjugate Fcj when an aplanatic ideal lens is included at the pupil conjugate Pcj position) is 0.450. A maximum diameter of the reflection surfaces is 230 mm, and a maximum effective diameter of the refracting face is 106.3 mm.

TABLE 8

| Surface Number | Lens Number | Radius of curvature (mm) | Surface separation (mm) | Refractive index Nd, dispersion Vd | Effective radius (mm) |
|---|---|---|---|---|---|
| Subject | eye pupil | ∞ | ∞ | | |
| 1 | D | ∞ | 34.44765 | | 1.00 |
| 2 | L01 | −70.00000 | 15.66477 | 1.59319, 67.9 | 43.08 |
| 3 | | −54.42441 | 25.58099 | | 47.29 |
| 4 | Virtual surface | −58.73975 | 75.32132 | | 57.14 |
| 5 (aspherical surface) | First reflection surface | −125.75112 | −75.32132 | | 115.00 |
| 6 (aspherical surface) | Second reflection surface | −58.73975 | 50.00000 | | 36.25 |
| 7 | L02 | −104.90424 | 3.00000 | 1.76182, 26.6 | 39.11 |
| 8 | | 1633.52922 | 14.26565 | | 41.32 |
| 9 | L03 | −70.05541 | 14.52143 | 1.49782, 82.6 | 41.40 |
| 10 | | −49.23060 | 139.45870 | | 42.89 |
| 11 | L05 | 100.00000 | 20.00000 | 1.80809, 22.8 | 53.15 |
| 12 | | 89.39939 | 11.94711 | | 48.59 |
| 13 | L06 | 453.67848 | 11.97727 | 1.59319, 67.9 | 48.61 |
| 14 First pupil conjugate | | −188.86514 | 279.13644 | | 48.62 |

The aspherical surface coefficients representing the aspherical surface of surface 5 are as follows.
A=−0.119695E−08
B=+0.639162E−12
C=+0.383380E−16
D=−0.483487E−20
E=+0.121159E−24

The aspherical surface coefficients representing the aspherical surface of surface 6 are as follows.
A=−0.449100E−06
B=+0.253492E−08
C=−0.308466E−11
D=+0.171588E−14
E=−0.458747E−18

Figure 24:
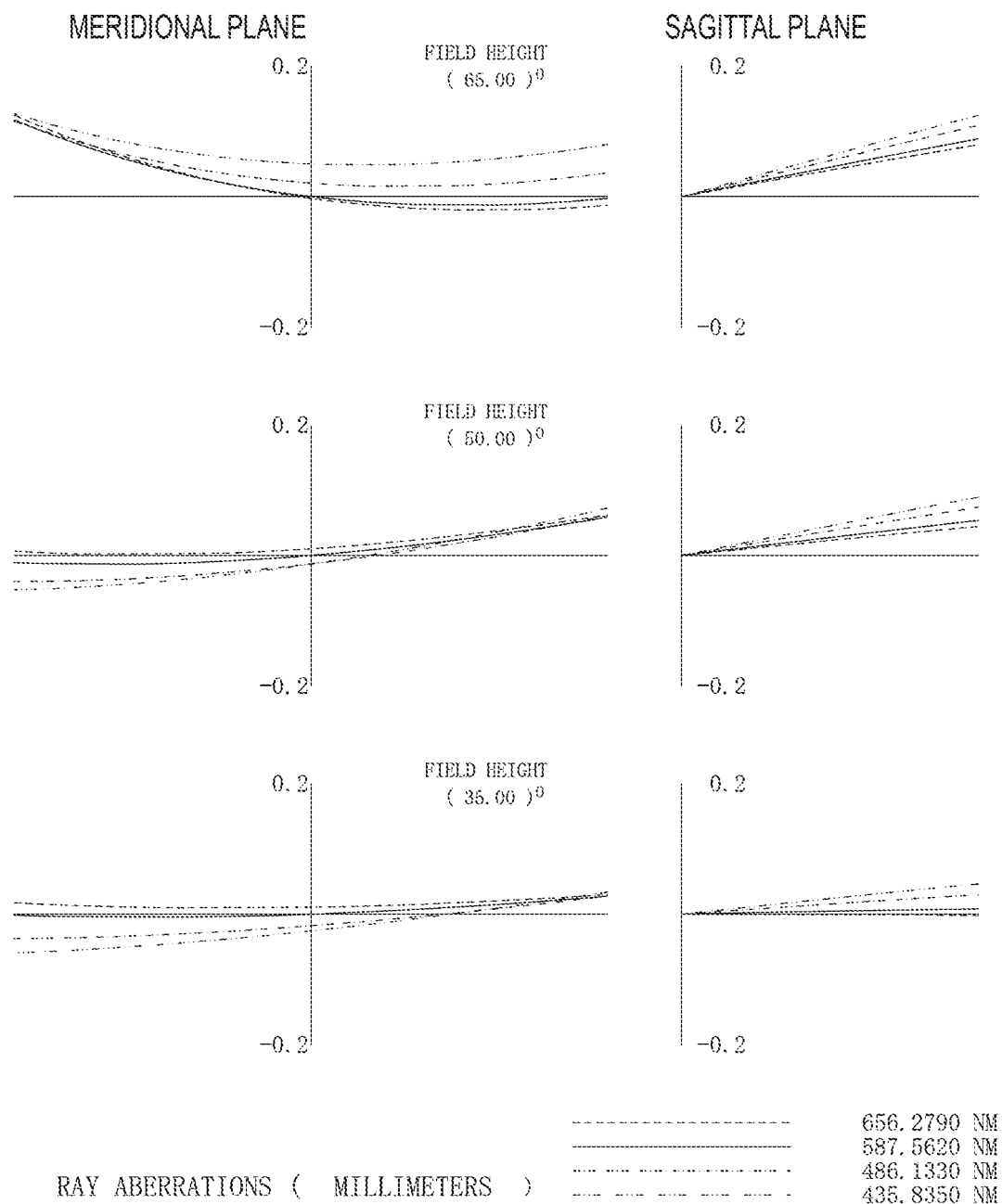
FIG. 24 is a lateral aberration diagram of the second optical system according to practical example 3-3.

FIG. 24 shows lateral aberration diagrams of the second optical system 28A2 configured in accordance with the elements in Table 8.

In the aberration diagrams shown in FIG. 24, the same as above, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 24, in the second optical system 28A2 according to practical example 3-3, variations in aberration for lights in the visible wavelength region are suppressed and are excellently corrected.

The following Table 9 shows the corresponding values in the conditional expressions (1) to (4) described above for the respective configurations of practical examples 1-1 to 3-2.

TABLE 9

| | | β1 | β2 | M1 | M2 | L1 | L2 | Conditional expression (1) | Conditional expression (2) | Conditional expression (3) | Conditional expression (3) |
|---|---|---|---|---|---|---|---|---|---|---|---|
| Practical example 1-1 | Center | 4.88 | | 0.3 | | 565 | | 0.61 | 6.97 | 11.5 | 1.099 |
| Practical example 1-2 | Surrounding | | 4.9 | | 0.57 | | 521 | | | | |
| Practical example 1-1 | Center | 4.88 | | 0.3 | | 565 | | 0.5 | 6.97 | 14 | 1 |
| Practical example 1-3 | Surrounding | | 3.92 | | 0.72 | | 565 | | | | |
| Practical example 2-1 | Center | 3.95 | | 0.27 | | 550 | | 0.46 | 5.4 | 11.7 | 1 |
| Practical example 2-2 | Surrounding | | 5.64 | | 0.52 | | 549 | | | | |
| Practical example 3-1 | Center | 7.24 | | 0.25 | | 590 | | 0.73 | 9.64 | 13.3 | 1.04 |
| Practical example 3-2 | Surrounding | | 6.4 | | 0.52 | | 565 | | | | |

In the exemplary embodiments described above, polygon mirrors and mirror galvanometers are mentioned as examples of the first optical scanner 22, the second optical scanner 24 and the third optical scanner 29, but this is not limiting. For example, alternative optical elements that are capable of scanning scanned light in the Y direction may be employed. For example, micro-electromechanical systems (MEMS) mirrors, rotating mirrors, prisms and oscillating mirrors can be mentioned.

Obviously, the scanning devices described above may perform similar scanning with the X direction and the Y direction exchanged.

In a catadioptric optical system that is capable of imaging surrounding regions with an ultrawide angle, stray light may be prevented by providing a shading screen in a central region containing the optical axis. Stray light may be reduced by limiting the illumination regions of scanned light from the SLO unit 18 and the OCT unit 20 to annular regions of the imaging field of view.

In the present exemplary embodiment, an example is described in which the control device 16 is realized by a computer. However, the control device 16 is not limited to being realized by a computer and may be realized by alternative hardware structures.

The present invention has been described using an exemplary embodiment, but the technical scope of the present invention is not to be limited to the scope described in the above exemplary embodiment. Numerous modifications and improvements may be applied to the above exemplary embodiment within a scope not departing from the gist of the invention, and modes to which these modifications and/or improvements are applied are to be encompassed by the technical scope of the invention. All references, patent applications and technical specifications cited in the present specification are incorporated by reference into the present specification to the same extent as if the individual references, patent applications and technical specifications were specifically and individually recited as being incorporated by reference.

EXPLANATION OF THE REFERENCE SYMBOLS

10 Ophthalmic imaging apparatus
12 Subject eye
12A Imageable region
12A1 First imageable region
12A2 Second imageable region
16 Control device
19 Scanning device
28 Common optical system
28A Optical system
A External illumination angle

The invention claimed is:

1. An ophthalmic apparatus comprising:
    a first optical system that acquires an image of a predetermined region of a subject eye; and
    a second optical system that includes a catadioptric optical unit and that acquires an image of a surrounding portion of the predetermined region,
    wherein the shape of the image of the surrounding portion is an annular shape centered on the optical axis of the ophthalmic apparatus, the predetermined region contains the optical axis, and there is an overlap between the image of the predetermined region according to the first optical system and the annular image of the surrounding portion of the predetermined region according to the second optical system, the overlap including a boundary between the images.

2. The ophthalmic apparatus according to claim 1, wherein the catadioptric optical unit includes:
    a first reflection surface that includes an aperture portion centered on an optical axis of the ophthalmic apparatus and reflects light from the subject eye; and
    a second reflection surface that includes an aperture portion centered on the optical axis of the ophthalmic apparatus and reflects light reflected from the first reflection surface, the second reflection surface reflecting the light to the opposite side from a side of the second reflection surface at which the subject eye is disposed.

3. The ophthalmic apparatus according to claim 2, wherein the first optical system and the second optical system respectively form a pupil conjugate position that is conjugate with a position of a pupil of the subject eye at a position at an opposite side at which the subject eye is disposed.

4. The ophthalmic apparatus according to claim 1, wherein:
the first optical system includes a first optical unit and a rear optical unit, and
the second optical system includes the catadioptric optical unit and the rear optical unit.

5. The ophthalmic apparatus according to claim 1, further comprising a replacement device that replaces the first optical unit with the catadioptric optical unit.

6. The ophthalmic apparatus according to claim 1, wherein:
the first optical system includes a first optical unit and a rear optical unit, and
the second optical system includes the catadioptric optical unit and a rear optical unit that differs from the rear optical unit of the first optical system.

7. The ophthalmic apparatus according to claim 6, further comprising a replacement device that replaces the first optical system with the second optical system.

8. The ophthalmic apparatus according to claim 3, wherein the first optical system and the second optical system satisfy the conditional expression:

$$0.2 < \beta 1 \cdot (1-M2)/\beta 2 \cdot (1-M1) < 1.0$$

in wherein $\beta 1$ represents an imaging magnification of the first optical system between a pupil position of the subject eye and a pupil conjugate position, M1 represents a distortion factor of a maximum field of view of a fundus conjugate image when an aplanatic ideal lens is included at the pupil conjugate position,
$\beta 2$ represents an imaging magnification of the second optical system between the pupil position of the subject eye and the pupil conjugate position, and M2 represents a distortion factor of the maximum field of view of the fundus conjugate image when the aplanatic ideal lens is included at the pupil conjugate position.

9. The ophthalmic apparatus according to claim 8, wherein $\beta 1$, $\beta 2$, M1 and M2 satisfy the conditional expressions:

$$2 < \beta 1/(1-M1) < 13$$

$$9 < \beta 2/(1-M2) < 17.$$

10. An ophthalmic apparatus comprising:
a first optical system that acquires an image of a predetermined region of a subject eye; and
a second optical system that includes a catadioptric optical unit and that acquires an image of a surrounding portion of the predetermined region,
wherein the second optical system is configured to enable incidence of light from the pupil of the subject eye into the catadioptric optical unit with an external illumination angle of at least 100°.

11. The ophthalmic apparatus according to claim 10, wherein optical elements of the first optical system and the second optical system are respectively aligned on a single optical axis.

12. An ophthalmic apparatus comprising:
a first optical system that acquires an image of a predetermined region of a subject eye; and
a second optical system that includes a catadioptric optical unit and that acquires an image of a surrounding portion of the predetermined region,
wherein each of the first optical system and the second optical system includes a common lens group with a positive refractive power overall, the common lens group including a surface with a negative refractivity at at least one surface.

13. The ophthalmic apparatus according to claim 12, wherein the ophthalmic apparatus satisfies the conditional expression:

$$0.8 < L1/L2 < 1.2$$

wherein L1 represents a distance from a pupil position of the subject eye to a pupil conjugate position with respect to the first optical system, and L2 represents a distance from the pupil position of the subject eye to a pupil conjugate position with respect to the second optical system.

14. The ophthalmic apparatus according to claim 12, wherein the ophthalmic apparatus satisfies the conditional expression:

$$1.0 \leq H1/H2 < 5.0$$

wherein H1 represents an effective aperture diameter of the first optical system in the plane of a pupil position at the subject eye, and H2 represents an effective aperture diameter of the second optical system in the plane of the pupil position at the subject eye.

\* \* \* \* \*